US009000136B2

(12) United States Patent
Kohara et al.

(10) Patent No.: US 9,000,136 B2
(45) Date of Patent: Apr. 7, 2015

(54) RECOMBINANT VACCINIA VIRUS HAVING HEPATITIS C VIRUS GENE

(75) Inventors: Michinori Kohara, Tokyo (JP); Fukashi Murai, Tsukuba (JP)

(73) Assignees: Tokyo Metropolitan Institute of Medical Science, Tokyo (JP); The Chemo-Sero-Therapeutic Research Institute, Kumamoto (JP)

( * ) Notice: Subject to any disclaimer, the term of this patent is extended or adjusted under 35 U.S.C. 154(b) by 391 days.

(21) Appl. No.: 12/736,079

(22) PCT Filed: Mar. 6, 2009
(Under 37 CFR 1.47)

(86) PCT No.: PCT/JP2009/054825
§ 371 (c)(1),
(2), (4) Date: Feb. 2, 2011

(87) PCT Pub. No.: WO2009/110644
PCT Pub. Date: Sep. 11, 2009

(65) Prior Publication Data

US 2011/0275139 A1 Nov. 10, 2011

(30) Foreign Application Priority Data

Mar. 7, 2008 (JP) ................................ 2008-057515
Nov. 18, 2008 (JP) ................................ 2008-294361

(51) Int. Cl.
*C07H 21/02* (2006.01)
*C12Q 1/70* (2006.01)
*A61K 39/29* (2006.01)
*C12N 15/863* (2006.01)
*A61K 39/00* (2006.01)

(52) U.S. Cl.
CPC .. *C12N 15/8636* (2013.01); *C12N 2710/24143* (2013.01); *A61K 2039/525* (2013.01)

(58) Field of Classification Search
USPC ........................................................ 435/235
See application file for complete search history.

(56) References Cited

U.S. PATENT DOCUMENTS

2005/0019347 A1* 1/2005 Sutter et al. ................ 424/199.1
2006/0134065 A1 6/2006 Fournillier
2009/0214587 A1 8/2009 Kohara et al.

FOREIGN PATENT DOCUMENTS

EP 1 710 300 A1 10/2006
JP 2003-064096 A 3/2003
JP 2005-502362 A 1/2005
WO 2006/013815 A1 2/2006
WO 2006/038742 A1 4/2006

OTHER PUBLICATIONS

Eisenbach et al., Immune responses agains HCV-NS3 after accidental infection with HCV-NS3 recombinant vaccinia virus Journal of Viral Hepatitis, 2007, 14: pp. 817-819.*
Kitabatake et al. SARS-CoV spike protein expressing recombinant vaccinia virus efficiently induces neutralizing antibodies in rabbits pre-immunized with vaccinia virus, Vaccine, 25: pp. 630-637.*
Tsukiyama et al., Activation of the CKI-CDK-Rb-E2F Pathway in full genome hepatitis C Virus-expressing Cells, The Journal of Biological Chemistry, 2004, 279(15), pp. 14531-14541.*
Rollier et al., Control of Heterologous Hepatitis C Virus Infection in Chimpanzees Is associated with Quality of Vaccine-induced peripheral T-helper immune response, Journal of Virology, 2004. 78(1): pp. 187-196.*
Heile et al., Evaluation of Hepatitis C Virus Glycoprotein E2 for vaccine Design: an endoplasmic reticulum-retained recombinant protein is superior to secreted recombinant protein and DNA-Based Vaccine candidates, Journal of Virology. 2000. 74(15): pp. 6885-6892.*
C. Eisenbach, et al., Immune responses against HCV-NS3 after accidental infection with HCV-NS3 recombinant vaccinia virus, Journal of Viral Hepatitis, 2007, vol. 14, pp. 817-819.
M. Kitabatake, et al., SARS-CoV spike protein-expressing recombinant vaccinia virus efficiently induces neutralizing antibodies in rabbits pre-immunized with vaccinia virus, Vaccine, 2007, vol. 25, pp. 630-637.
K. Shinoda, et al., Robust HIV-specific immune responses were induced by DNA vaccine prime followed by attenuated recombinant vaccinia virus (LC16m8 strain) boost, Clinical Immunology, 2006, vol. 119, pp. 32-37.
K. Watanabe, et al., Stability of recombinant vaccinia virus LC16m0 or LC16m8: Preserved laboratory attenuation markers and conserved expression of inserted HBsAg gene, Vaccine, vol. 7, Dec. 1989, pp. 499-502.
Database DDBJ/EMBL/GenBank [online], Accession No. AY045702 <http://www.ncbi.nlm.nih.gov/nuccore/15529110> Sep. 5, 2007 uploaded, Tsukiyama-Kohara, K., et al., Definition: Hepatitis C virus isolate HCR6, complete genome. [retrieved on May 14, 2009].
S. Funahashi, et al., Increased Expression In Vivo and In Vitro of Foreign Genes Directed by A-Type Inclusion Body Hybrid Promoters in Recombinant Vaccinia Viruses, Journal of Virology, Oct. 1991, vol. 65, No. 10, pp. 5584-5588.
N.Y. Jin, et al., Constructions of vaccinia virus A-type inclusion body protein, tandemly repeated mutant 7.5kDa protein, and hemagglutinin gene promoters support high levels of expression, Arch Virol, 1994, vol. 138, pp. 315-330.

(Continued)

*Primary Examiner* — Zachariah Lucas
*Assistant Examiner* — Barry A Chestnut
(74) *Attorney, Agent, or Firm* — McDermott Will & Emery LLP

(57) ABSTRACT

Provided is a recombinant virus which is efficacious in preventing the onset of hepatitis C infection and has a high safety. Also provided is a vaccine for hepatitis C virus which contains the recombinant virus. A recombinant vaccinia virus which can express hepatitis C virus gene. The hepatitis C virus vaccine as described above contains the recombinant virus as described above.

5 Claims, 11 Drawing Sheets
(2 of 11 Drawing Sheet(s) Filed in Color)

(56) References Cited

OTHER PUBLICATIONS

T. Wakita, et al., Efficient Conditional Transgene Expression in Hepatitis C Virus cDNA Transgenic Mice Mediated by the Cre/loxP System, The Journal of Biological Chemistry, vol. 273, No. 15, Apr. 10, 1998, pp. 9001-9006.
K. Inoue, et al., Evaluation of a Cyclophilin Inhibitor in Hepatitis C Virus-Infected Chimeric Mice In Vivo, Hepatology, Apr. 2007, vol. 45, No. 4, pp. 921-928.
Q. L. Choo, et al., Vaccination of chimpanzees against infection by the hepatitis C virus, Proc. Natl. Acad. Sci. USA, Feb. 1994, vol. 91, pp. 1294-1298.
M. Puig, et al., Immunization of chimpanzees with an envelope protein-based vaccine enhances specific humoral and cellular immune responses that delay hepatitis C virus infection, Vaccine, vol. 22, 2004, pp. 991-1000.
J. D. Abraham, et al., Comparative immunogenicity analysis of modified vaccinia Ankara vectors expressing native or modified forms of hepatitis C virus E1 and E2 glycoproteins, Vaccine, vol. 22, 2004, pp. 3917-3928.
G. A. Elmowalid, et al., Immunization with hepatitis C virus-like particles results in control of hepatitis C virus infection in chimpanzees, Proc. Natl. Acad. Sci., May 15, 2007, vol. 104, No. 20, pp. 8427-8432.
J. Youn et al., "Polyvalent Immunization Against Hepatitis B and C Viruses With Recombiant Vaccine Virus", The Tenth Annual Conference on Vaccine Research, May 2, 2007, Abstract of Oral Presentation, p. 67.
Susanne El Gogo et al., "Protective vaccination with heptitis C virus NS3 but not core antigen in a novel mouse challenge model", The Journal of Gene Medicine, Feb. 2008, vol. 10, No. 2, pp. 177-186.
Liz Alvarez-Lajonchere, et al, "Generation and characterization of recombinant vaccinia viruses expressing a hepatitis C virus Core protein, genotype 1b, individually or as a polyprotein", Biotecnologia Aplicada, Jul. 2007, vol. 24, No. 3-4, pp. 246-253.
Christoph Eisenbach, et al, "Multigenotype HCV-NS3 recombinant vaccinia viruses as a model for evaluation of cross-genotype immunity induced by HCV vaccines in the mouse", Vaccine, Jun. 12, 2006, vol. 24, No. 24, pp. 5140-5148.
K. Watanabe, et al, "Improved recombinant LC16m0 or LC16m8 vaccinia virus successfully expressing hepatitis B surfacce antigen", Vaccine, Elsevier Ltd., GB, Feb. 1, 1989, vol. 7, No. 1, pp. 53-59.
A Supplementary European Search Report, which was completed on May 16, 2012, in the prosecution of EP 09717492, which corresponds to the present application.
H. Yu et al., Immunity and protection by adoptive transfer of dendritic cells transfected with hepatitis C NS3/4A mRNA, Vaccine, vol. 25, pp. 1701-1711, 2007.
V. Chung et al., Development of Cell-Based Assays for In Vitro Characterization of Hepatitis C Virus NS3/4A Protease Inhibitors, Antimicrobial Agents and Chemotherapy, vol. 49, No. 4, pp. 1381-1390, Apr. 2005.
R. Ralston et al., Characterization of Hepatitis C Virus Envelope Glycoprotein Complexes Expressed by Recombinant Vaccinia Viruses, Journal of Virology, vol. 67, No. 11, pp. 6753-6761, Nov. 1993.

* cited by examiner

1. Amino acid sequences of H-2$^d$ CTL epitope

| Region | code | epitope name | References | | number of | HCR6 | |
|---|---|---|---|---|---|---|---|
| | | | aa position | sequence | aa | sequence | aa position |
| Core | 1 | C7-A10 | 133-142 | LMGYIPLVGA (SEQ ID NO:17) | 9 | LMGYIPLVGA (SEQ ID NO:17) | 133-142 |
| E1 | 1 | E1 315-322 | 315-322 | GHRVAWDM (SEQ ID NO:18) | 8 | GHRMAWDM (SEQ ID NO:18) | 315-322 |
| E2 | 1 | E2 565-574 | 565-574 | GGPPCDIGGV (SEQ ID NO:19) | 10 | GGPPCNIGGG (SEQ ID NO:20) | 565-574 |

2. Results from ELISPOT assay (BALB/c H-2$^d$)

RECOMBINANT VACCINIA VIRUS HAVING HEPATITIS C VIRUS GENE

CROSS REFERENCE TO PRIOR APPLICATIONS

This application is a U.S. National Phase application under 35 U.S.C. §371 of International Application No. PCT/JP2009/054825, filed on Mar. 6, 2009 and claims benefit of priority to Japanese Patent Application No. 2008-057515, filed on Mar. 7, 2008 and Japanese Patent Application No. 2008-294361, filed on Nov. 18, 2008. The International Application was published in Japanese on Sep. 11, 2009 as WO 2009/110644 A1 under PCT Article 21(2). All of these applications are herein incorporated by reference.

FIELD OF THE INVENTION

The present invention relates to a prophylactic agent and a therapeutic agent for hepatitis C. More specifically, the present invention relates to a recombinant vaccinia virus that can express a hepatitis C virus gene, and a prophylactic agent and a therapeutic agent for hepatitis C comprising the recombinant vaccinia virus.

BACKGROUND OF THE INVENTION

There are more than two million people infected with hepatitis C virus (HCV) in Japan, among which about 36,000 people develop hepatocarcinoma every year where most of the cancer patients result in death. Currently, interferon (IFN) is used as the only effective anti-HCV drug, which has limited effect and serious side-effects. Thus, there is a demand for development of a safer and more effective drug. Furthermore, since aging of the infected people increases the risk of developing cancer, there is a need for urgent remedy.

At the current moment, drugs such as nucleic acid analogs, protease inhibitors and the like that suppress viral replication of HCV have been developed and used for treatment. In treatment using these drugs, however, a drug-resistant virus is likely to emerge, and complete elimination of the virus is difficult in view of the mechanisms of this action of the virus, thus a lifelong medication is necessary. In such circumstances, there has been a strong desire for establishment of a curative therapy that allows withdrawal and relief from lifelong medication.

The present inventors have established various experimental model systems, namely, research sources in association with HCV studies by preparing an infectious cDNA clone of HCV and establishing infected animals such as HCV-infectious transgenic mice and human liver chimeric mice and the like (e.g., see Non-patent Document 1). The major features of HCV infection include establishment of persistent infection at a high rate and progress to chronic hepatitis. The present inventors have gone through keen analyses and examinations over the years using the above-mentioned experimental model systems and the like by looking at this mechanism of action in terms of acquisition of immunological tolerance and breakdown thereof (e.g., see Non-patent Document 2).

Numerous attempts to develop a vaccine for preventing HCV infection have been made heretofore but so far none of them provided complete prevention of infection (e.g., see Non-patent Documents 3, 4, 5 and 6).

Non-patent Document 1: Wakita T., et al., J. Biol. Chem., 1998, vol. 273, p9001-9006

Non-patent Document 2: Inoue K., et al., Hepatology, 2007, vol. 45, p921-928

Non-patent Document 3: Choo Q L., et al., Pros. Natl. Acad. Sci. 1994, vol. 91, 1294-1298

Non-patent Document 4: Puig M., et. al., Vaccine 2004, vol. 22, 991-1000

Non-patent Document 5: Abraham J D., Vaccine 2004, vol. 22, 3917-3928

Non-patent Document 6: Elmowalid G A., et. al., Pros. Natl. Acad. Sci. 2007, vol. 104, 8427-8432

DISCLOSURE OF THE INVENTION

The objective solved by the present invention is to provide a therapeutic agent or a prophylactic agent comprising a recombinant vaccinia virus efficacious in preventing the onset of hepatitis C infection.

The present inventors have further gone through keen research based on the results from the above-mentioned analyses and examinations on HCV infection, and came up with an idea that strong immune activation brought about by a recombinant vaccinia vaccine can result in a potent hepatitis C infection prevention method. Moreover, the present inventors also considered that strong activation of the immunological elimination system brought about by a recombinant vaccinia vaccine or the like could provide a potent hepatitis C curative therapy, and thus aiming for complete control of the pathological conditions of a poorly curable viral disease seemed to be possible. The present inventors have also devoted themselves to studies in order to solve the above problem based on their findings from many years of research on viral infections. As a result, they succeeded in preparing a recombinant vaccinia virus that is efficacious in preventing the onset of hepatitis C infection, thereby accomplishing the present invention.

Thus, the present invention is as follows.

(1) A recombinant vaccinia virus comprising an expression promoter and the entire or a part of cDNA of hepatitis C virus genome.

An example of a vaccinia virus includes LC16m8 strain. Examples of cDNAs of hepatitis C virus genome include those coding for a structural protein of hepatitis C virus or a nonstructural protein of hepatitis C virus, and those coding for both the structural protein of hepatitis C virus and the nonstructural protein of hepatitis C virus.

Specifically, DNAs of (a) to (f) below are exemplified as the cDNAs of hepatitis C virus genome:

(a) DNA having the nucleotide sequence represented by SEQ ID NO:1;

(b) DNA that hybridizes with DNA having a nucleotide sequence complementary to the nucleotide sequence represented by SEQ ID NO:1 under stringent conditions, and that codes for a structural protein of hepatitis C virus;

(c) DNA having the nucleotide sequence represented by SEQ ID NO:2;

(d) DNA that hybridizes with DNA having a nucleotide sequence complementary to the nucleotide sequence represented by SEQ ID NO:2 under stringent conditions, and that codes for a nonstructural protein of hepatitis C virus;

(e) DNA having the nucleotide sequence represented by SEQ ID NO:3; and (f) DNA that hybridizes with DNA having a nucleotide sequence complementary to the nucleotide sequence represented by SEQ ID NO:3 under stringent conditions, and that codes for a structural protein and a nonstructural protein of hepatitis C virus.

Moreover, an example of the expression promoter contained in the recombinant vaccinia virus of the present invention includes a hybrid promoter. Specifically, DNAs of (a) and (b) below are exemplified as a nucleotide sequence of the hybrid promoter:

(a) DNA having the nucleotide sequence represented by SEQ ID NO:4; and (b) DNA that hybridizes with DNA having a nucleotide sequence complementary to the nucleotide sequence represented by SEQ ID NO:4 under stringent conditions and that has a promoter activity.

(2) A pharmaceutical composition comprising the recombinant vaccinia virus according to (1) above.

The pharmaceutical composition may be used as a prophylactic agent or a therapeutic agent for hepatitis C.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODES FOR CARRYING OUT THE INVENTION

Figure 1:
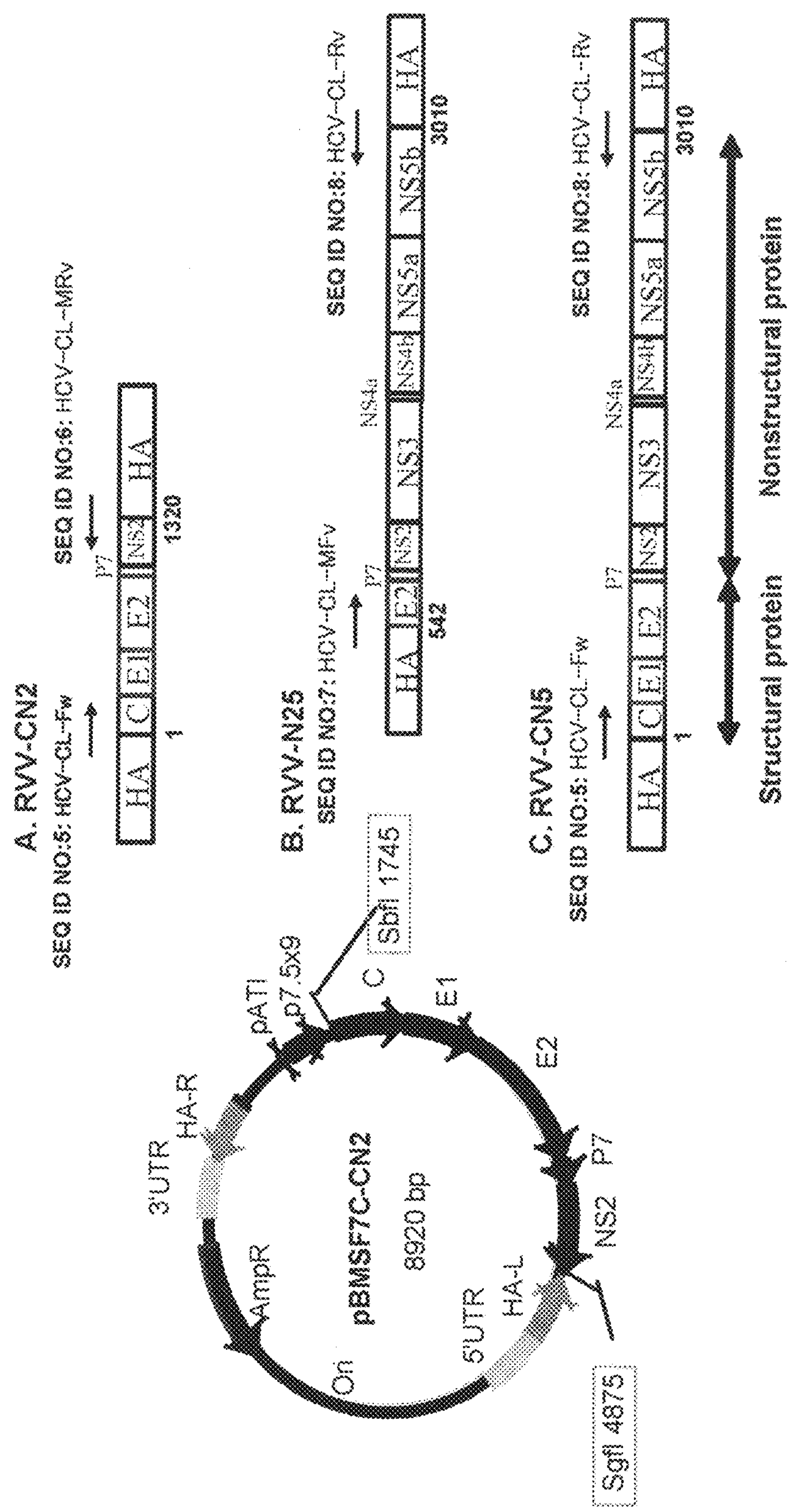
FIG. 1 shows a gene structure of a plasmid used for preparing a HCV recombinant vaccinia virus.

Hereinafter, a recombinant vaccinia virus according to the present invention and an application thereof will be described in more detail although the scope of the present invention should not be limited to these descriptions, and appropriate modification may be performed in a manner apart from the following examples without departing from the scope of the invention.

The present specification incorporates the content of the specifications of Japanese Patent Application Nos. 2008-57515 (filed on Mar. 7, 2008) and 2008-294361 (filed on Nov. 18, 2008), to which the present application claims priority.

Additionally, the patent documents, non-patent documents and other publications cited herein are incorporated herein by reference.

1. Summary

Among various vaccines, live vaccines are some of particularly efficacious vaccines, but development of an attenuated vaccine for a new virus is generally known to require a very long period of time, which is likely to be the case for HCV as well.

A gene engineering technique for preparing a recombinant vaccinia virus (RVV) as a live vaccine is one of the known techniques employed in such a case. For example, recombinant vaccinia viruses for rabies virus or rinderpest developed by the present inventors have been demonstrated to exert superior effects in preventing the onset of infection in field tests and the like (e.g., see Tsukiyama K., et al., Arch. Virol., 1989, vol. 107, p. 225-235).

Moreover, the present inventors have succeeded in preparing a recombinant vaccinia virus that has cDNA of SARS-CoV, a known pathogen of atypical pneumonia SARS (WO2006/038742), and confirmed it to be a formulation having a superior prophylactic effect, which can be used for repeated administration (e.g., see Kitabatake M., et al., Vaccine, 2007, vol. 25, p. 630-63'7).

A vaccinia virus used as a recombinant parent for preparing RVV needs to be a vaccine strain that has established safety. Vaccinia virus strain LC16m8 (e.g., see Clinical Virology vol. 3, No. 3, 269, 1975) is known as such a vaccine strain. LC16m8 strain is derived from Lister strain and currently the only vaccine strain that has actually been administrated as a prophylactic vaccine whose safety and efficacy have been confirmed.

The present inventors also found, in the course of developing and studying recombinant vaccinia viruses against rinderpest, HIV, SARS-CoV and the like, that the use of a gene expression promoter that can highly enhance the antibody-producing ability and the cellular immunity-inducing ability is effective for the vaccinia virus of the present invention. Specifically, the present inventors found that pSFJ1-10 or pSFJ2-16 can be used as a preferable plasmid vector (e.g., see Jin N-Y, et al., Arch. Virol. 1994, vol. 138, p. 315-330, Elmowalid G A., et. al., Pros. Natl. Acad. Sci. 2007, vol. 104, 8427-8432; Arch. Virol. 138, 315-330, 1994; Japanese Patent Laid-Open Application No. 6-237773, etc.).

As a result, the present inventors succeeded in preparing a HCV recombinant vaccinia virus by integrating a gene coding for a nonstructural protein of HCV and/or a gene coding for a structural protein of HCV together with a promoter into a vaccinia virus.

A parental virus of a recombinant vaccinia virus of the present invention is a vaccinia virus as described above. A recombinant vaccinia virus of the present invention has cDNA of HCV integrated into the genome of the vaccinia virus. An expression unit obtained by cloning the entire gene regions encoding the HCV protein, the outer capside protein region, or the gene of the nonstructural protein region associated with replication is transferred into a vaccinia virus vector. This expression unit is introduced into the HA-coding region of the vaccinia virus. Since foreign gene transfer into the HA-coding region has no influence on the proliferation activity of the vaccinia virus, as is already known, a safe vaccine strain having weak proliferating ability can be used as the parental virus (Vaccine 12, 675-681, 1994).

Live recombinant vaccinia vaccines against rabies virus, rinderpest virus and the like have been field-tested, where their excellent prophylactic effects have been proved against the onset of respective infections.

The present inventors prepared a recombinant vaccinia virus (RVV) by inserting the entire gene coding for hepatitis C virus (HCV) protein, a gene coding for the outer capside protein region, or a gene coding for a replication-associated nonstructural protein region downstream from a hybrid promoter, and integrating these genes into the hemagglutinin (HA) gene region of an attenuated vaccinia virus strain.

The hybrid promoter includes a poxvirus A-type inclusion (ATI) promoter and a vaccinia virus 7.5 kDa protein (p7.5) early expression promoter with multiple repeats (see Jin N-Y, et al., Arch. Virol. 1994, vol. 138, p. 315-330). This promoter was developed by and available from Dr. Hisatoshi Shida at Hokkaido University.

The prepared RVV was used to infect an animal cell, by which abundant expression of HCV protein as well as earlier production of a high-titer antibody against HCV were confirmed by vaccination to an animal individual. Additionally, cellular immunity was also confirmed to be activated upon vaccination to an animal individual by ELISPOT assay, thereby accomplishing the present invention.

2. Preparation of HCV Recombinant Vaccinia Virus

The entire gene coding for hepatitis C virus (HCV) protein, a gene coding for the outer capside protein region, and a gene coding for a replication-associated nonstructural protein region have already been cloned and inserted into a plasmid. Hence, a gene contained in the recombinant virus of the present invention can be obtained according to a usual gene engineering technique. For example, a nucleic acid synthesis method using a generally-used DNA synthesizer may be employed as such a gene engineering technique. Moreover, after isolating or synthesizing a gene sequence as a template, a PCR method may be employed in which primers specific to each gene are designed to amplify the gene sequences with a PCR device or a gene amplification method using a cloning vector. The above-mentioned methods may readily be carried out by those skilled in the art according to Molecular cloning 2nd Ed. Cold Spring Harbor Laboratory Press (1989) or the like. The obtained PCR product may be purified according to a known method.

In a preferred embodiment of the present invention, the HCV gene inserted into the above-described plasmid (Genotype 1b; Nucleotide Number: 1-9611; DDBJ/EMBL/GenBank accession number: AY045702) may be used as a template. Thus, HCV gene cDNA is used as a template with HCV gene-specific primers to perform PCR, thereby preparing each gene region of HCV. According to the present invention, the entire gene regions of HCV, a gene coding for the structural protein region of the outer capside protein and a gene coding for the replication-associated nonstructural protein region are referred to as “CN5”, “CN2” and “N25”, respectively.

The nucleotide sequences of CN2, N25 and CN5 are represented by SEQ ID NOS:1, 2 and 3, respectively. Other than the DNAs of the sequences represented by SEQ ID NOS:1 to 3, the following DNAs may also be used for the present invention.

DNA that hybridizes with DNA having a nucleotide sequence complementary to the nucleotide sequence represented by SEQ ID NO:1 under stringent conditions, and that codes for a structural protein of hepatitis C virus (mutant DNA of CN2);

DNA that hybridizes with DNA having a nucleotide sequence complementary to the nucleotide sequence represented by SEQ ID NO:2 under stringent conditions, and that codes for a nonstructural protein of hepatitis C virus (mutant DNA of N25);

DNA that hybridizes with DNA having a nucleotide sequence complementary to the nucleotide sequence represented by SEQ ID NO:3 under stringent conditions, and that codes for a structural protein and a nonstructural protein of hepatitis C virus (mutant DNA of CN5).

Herein, the phrase “coding for a structural protein of hepatitis C virus” means that the gene codes for a protein constituting the outer capside of the virus, specifically, the gene codes for at least the core region, E1 region and E2 region (FIG. 1A). Furthermore, the phrase “coding for a nonstructural protein of hepatitis C virus” means that the gene codes for a protein produced in the cell upon propagation of the virus, specifically, the gene codes for at least NS2 region, NS3 region, NS4a region, NS4b region, NS5a region and NS5b region (FIG. 1B).

In addition, the above-described genes coding for the structural protein and the nonstructural protein comprise the full-length sequence as well as a partial sequence thereof. In the case of CN2, it may not necessarily be a full-length sequence and may be a part thereof as long as it contains all or any of the core region, E1 region and E2 region. For example, E1 region (589-1164) and E2 region (1165-2253) of the nucleotide sequence represented by SEQ ID NO:1 may be used. In the case of N25, it may not necessarily be a full-length sequence and may be a part there of as long as it contains all or any of NS2 region, NS3 region, NS4a region, NS4b region, NS5a region and NS5b region. For example, NS2 region (805-1455) and NS3 region (1456-3348) of the nucleotide sequence represented by SEQ ID NO:2 may be used. In the case of CN5, it may not necessarily be a full-length sequence and may be a part thereof as long as it contains all or any of the core region, E1 region, E2 region, NS2 region, NS3 region, NS4a region, NS4b region, NS5a region and NS5b region. For example, E1 region (589-1164), E2 region (1165-2253), NS2 region (2443-3093) and NS3 region (3094-4986) of the nucleotide sequence represented by SEQ ID NO:3 may be used.

The above-described mutant DNA may be obtained by chemical synthesis, or it may alternatively be obtained from a cDNA library or a genome library by a known hybridization method such as colony hybridization, plaque hybridization, Southern blot or the like using DNA having the nucleotide sequence represented by any of SEQ ID NOS:1-3 or a fragment thereof as a probe. Examples of stringent conditions for the above-mentioned hybridization include 0.1×SSC to 10×SSC, 0.1% to 1.0% SDS and 20° C. to 80° C. More specifically, after performing prehybridization at 37° C. to 56° C. for 30 minutes or longer, washing is carried out for 1 to 3 times in 0.1×SSC, 0.1% SDS at room temperature for 10 to 20 minutes. For specific procedure of the hybridization method, reference may be made to “Molecular Cloning, A Laboratory Manual 2nd ed.” (Cold Spring Harbor Press (1989)) or the like.

Moreover, DNA (mutant DNA of CN2) that has 50% or more, 60% or more, 70% or more, 80% or more, 90% or more, 95% or more, 98% or more or 99% or more homology with the nucleotide sequence represented by SEQ ID NO:1 and that codes for the structural protein of hepatitis C virus, DNA (mutant DNA of N25) that has 50% or more, 60% or more, 70% or more, 80% or more, 90% or more, 95% or more, 98% or more or 99% or more homology with the nucleotide sequence represented by SEQ ID NO:2 and that codes for the nonstructural protein of hepatitis C virus, and DNA (mutant DNA of CN5) that has 50% or more, 60% or more, 70% or more, 80% or more, 90% or more, 95% or more, 98% or more or 99% or more homology with the nucleotide sequence represented by SEQ ID NO:3 and that codes for the nonstructural protein and structural protein of hepatitis C virus may be used.

A promoter contained in the recombinant vaccinia virus of the present invention is a hybrid promoter consisting of a poxvirus A-type inclusion (ATI) promoter and a vaccinia virus 7.5 kDa protein (p7.5) early expression promoter with multiple repeats included in the hemagglutinin (HA) gene region of the vaccinia virus. This promoter may be linked to an appropriate plasmid, for example, pBMSF7C (Arch. Virol. 138, 315-330, 1994; Japanese Patent Laid-Open Application No. 6-237773).

A nucleotide sequence of a hybrid promoter that can be used for the present invention is represented by SEQ ID NO:4. Besides DNA having the nucleotide sequence represented by SEQ ID NO:4, DNA that hybridizes with DNA having a nucleotide sequence complementary to the nucleotide sequence represented by SEQ ID NO:4 under stringent conditions and that has a promoter activity may also be used for the present invention. The "stringent conditions" are the same as describe above. The phrase "having a promoter activity" means to have an activity for transcripting a gene coding for a structural protein or a nonstructural protein.

A protein may be mass-expressed by this hybrid promoter in a completely sugar-modified form through early to late vaccinia virus infection. According to the present invention, a plasmid vector having HCV gene (CN5) inserted downstream from a pBMSF7C promoter is referred to as pBMSF7C-CN5. Moreover, according to the present invention, a plasmid vector having an outer capside protein region gene (CN2) inserted downstream from a pBMSF7C promoter is referred to as pBMSF7C-CN2. Furthermore, a plasmid vector having a nonstructural protein gene (N25) inserted downstream from pBMSF7C promoter is referred to as pBMSF7C-N25.

These plasmid vectors are transferred into a vaccinia virus as a host to prepare a recombinant vaccinia virus. For transfer into the host plasmid vector, any known technique may be employed. For example, any one of plasmid vectors pBMSF7C-CN5, pBMSF7C-CN2 and pBMSF7C-N25 can be introduced into an animal cell infected with an attenuated vaccinia virus strain LC16m8 to induce homologous recombination in the hemagglutinin (HA) gene region of the vaccinia virus to prepare recombinant vaccinia viruses (RVV-CN5, RVV-CN2 and RVV-N25) expressing the respective HCV proteins.

The vaccinia virus strain LC16m8 used for preparing RVV is an attenuated strain that may proliferate in an animal individual but has extremely low proliferating property in the nerve cells. This strain is approved as a smallpox vaccine in Japan and no serious side-effect has occurred from vaccination to approximately 50,000 children (research report by the smallpox vaccination research group at the Ministry of Health and Welfare, Clinical Virology vol. 3, No. 3, 269, 1975). On the other hand, its immunity-inducing ability is reported to be equivalent to that of Lister strain, i.e., the parent strain, and thus LC16m8 strain is a safe and effective vaccine.

Since the prepared RVV-CN5, RVV-CN2 and RVV-N25 have the HCV protein gene inserted into the HA gene region of the vaccinia virus, expression of HA protein is defected and thus no hemagglutination is caused. Accordingly, RVV-CN5, RVV-CN2 and RVV-N25 are used to infect animal cells, and RVV is screened using agglutination reaction of chicken erythrocyte with the resulting plaque as the indicator. The RVV of interest may be obtained by selecting white plaques in which no hemagglutination is observed.

Gene transfer of HCV in the virus obtained from the white plaques may be confirmed by performing PCR using the virus genome as a template and HCV gene-specific primers.

Expression of HCV protein may be confirmed by Western blot method using animal cells infected with RVV-CN5, RVV-CN2 and RVV-N25 as samples. Here, the antibody used may be obtained by purifying IgG with Protein G from an antiserum raised by immunization with an HCV polypeptide (J. Biol. Chem. 279:14531-14541, 2004).

Other than the HA gene region, thymidine kinase (TK) gene region is generally used as the insertion site for the gene of interest upon preparation of RVV but insertion of the gene of interest into the TK gene region is known to lower the RVV proliferation due to the defect in TK expression. On the other hand, the defect in HA protein expression is reported to have little effect on the RVV proliferation (Vaccine 12, 675-681, 1994). Therefore, according to the present invention, the insertion site of the gene of interest is preferably the HA gene region.

3. Pharmaceutical Composition for Preventing or Treating Hepatitis C

The present invention provides a prophylactic and therapeutic agent (a pharmaceutical composition) for hepatitis C comprising the above-described recombinant vaccinia virus.

A pharmaceutical composition of the present invention may be introduced into an organism by any known method such as intramuscular, intraperitoneal, intradermal or subcutaneous injection; nasal, buccal or lung inhalation; or oral administration. Additionally, a recombinant virus contained in a pharmaceutical composition of the present invention may be used in combination with an existing antiviral drug (for example, interferon). An embodiment of combinational use is not particularly limited, and the recombinant virus of the present invention and the existing antiviral drug may be introduced into an organism by a method in which both are administered simultaneously or by a method in which one is administered after the other at a certain interval.

Moreover, the pharmaceutical composition of the present invention may be blended with a known pharmaceutically acceptable carrier such as an excipient, a bulking agent, a binder and a lubricant, a buffer, a tonicity agent, a chelating agent, a colorant, a preservative, a fragrance, a flavoring agent, a sweetening agent or the like.

The pharmaceutical composition of the present invention may orally or parenterally be administered according to its form, for example, as an orally administered agent such as a tablet, a capsule, a powdered agent, a granular agent, a pill, a solution, syrup or the like, or a parenterally administered agent such as an injection, a topical agent, a suppository, an eye drop or the like. Preferably, it is, for example, a local injection such as an intradermal, intramuscular or intraperitoneal injection.

Although the dosage is appropriately chosen according to the type of the active element, administration route, administration target, age, weight, sex and symptoms of the patient and other conditions, the daily dosage of the virus is about 1,000-1,000,000,000 PFU (plaque forming units) and preferably about 100,000-100,000,000 PFU in the case of oral administration, while it is about 100-1,000,000,000 PFU and preferably about 1,000-100,000,000 PFU in the case of parenteral administration. The virus may be administered once or several times a day.

The recombinant virus of the present invention may be used as a vaccine for preventing or treating hepatitis C. Furthermore, development of a vaccine against HCV to date is based on the research focusing on antibodies against HCV and cytotoxic T cells (CTL). Therefore, the antibody titer or the cellular immunity activity as a vaccine is preferably measured beforehand.

For example, the antibody titers against the prepared RVV-CN5, RVV-CN2, RVV-N25 or LC16m8 strain, i.e., the parent strain, may be obtained by vaccinating a rabbit with the virus strain, collecting the sera over time, and measuring the ELISA value against HCV in the sera. In the sera of the rabbit vaccinated with RVV-CN5- or RVV-CN2, antibody titers against HCV increased after four weeks following the vaccination.

In addition, the cellular immunity activity can be measured by vaccinating a mouse with RVV-CN5, RVV-CN2, RVV-N25 or LC16m8 strain, i.e., the parent strain, isolating the spleen cells from the immunized mouse, and determining whether or not HCV-specific CTL is induced by ELISPOT assay. According to the present invention, when the spleen cells derived from RVV-CN5-vaccinated BALB/c mouse were stimulated with a synthetic peptide of a $H\text{-}2^d$-restricted E1-specific CTL epitope sequence, INF-γ-producing cells of nearly ten times the control were detected. Accordingly, RVV-CN5 vaccination was found to induce E1-specific CTL in BALB/c mice.

Thus, HCV-RVVs prepared by the present inventors have been confirmed to induce humoral and cellular immunity against HCV.

The present invention will be described more specifically by the following examples. These examples are for illustration only and should not limit the scope of the present invention.

Example 1

Preparation of Recombinant Vaccinia Virus

The entire gene regions (CN5), the outer capside protein region (CN2) and the gene region of the replication-associated nonstructural protein region (N25) of hepatitis C virus (DDBJ/EMBL/GenBank accession number; AY045702) were integrated into SbfI and SgfI Sites of pBMSF7C plasmid (Japanese Patent Laid-Open Application No. 6-237773) to prepare plasmid vectors pBMSF7C-CN5, pBMSF7C-CN2 and pBMSF7C-N25 having the HCV genes inserted downstream from the ATI·p7.5 hybrid promoter in hemagglutinin (HA) gene region (FIG. 1).

Primary cultured kidney cells were seeded into a T175 flask. Once the cells reached to confluence, the attenuated vaccinia virus strain LC16 m8 was used for infection at moi=10 and at 30° C. for 2 hours. Here, moi (multiplicity of infection) refers to PFU per cell. Following infection, the virus solution was removed by suction, and the cells were washed with PBS(−). Then, after treatment with 0.05% trypsin/0.5 mM EDTA/PBS(−) and washing with 10% FCS/MEM medium, PBS(−) and HeBS buffer, the cells were suspended in 600 μl HeBS buffer. 40 μg each of plasmid vectors pBMSF7C-CN5, pBMSF7C-CN2 and pBMSF7C-N25 was diluted using a HeBS buffer to obtain a total amount of 200 μl, which was added to and mixed with the cell suspension and left to stand on ice for 10 minutes. The cell suspension added with the plasmid vector was transferred to a 0.4 cm cuvette to perform electroporation (0.2 kV, 960 μF) using an electroporator (BIO-RAD). After electroporation, 1 ml of 10% FCS/MEM medium was immediately added to the cell suspension for dilution. This cell suspension was added to RK13 cell or primary cultured kidney cell that had been seeded into a T175 flask and cultured at 30° C. for 24 hours.

After 24 hours of cultivation, the culture supernatant was removed by suction and the cells were washed with PBS(−). Next, treatment with 0.05% trypsin/0.5 mM EDTA/PBS(−) was performed and then the cells were suspended in a 10% FCS/MEM medium. The cell suspension was collected, subjected to ultrasonication (30 sec×4 times) in cold water and then centrifuged (2000 rpm, 10 min). The resulting supernatant was used as a virus solution. The virus solution was diluted in 10% FCS/MEM medium, and used to infect the primary cultured kidney cell that had been seeded onto a 100 mm dish at 30° C. for an hour. The virus solution was removed by suction, and then the cells were washed with PBS(−). 10% FCS/0.5% methylcellulose/MEM medium was added for cultivation at 30° C. for 72 hours. After 72 hours of cultivation, the supernatant was removed by suction and washed with PBS(−). A chicken erythrocyte solution diluted in PBS(+) was added to the 100 mm dish for cultivation at 37° C. for 30 minutes. The erythrocyte solution was removed by suction and then the cells were washed twice with PBS(−). Plaques onto which chicken erythrocyte was unadsorbed were collected using a pipetman. HCV gene transfer in the collected plaques was confirmed by PCR and gene sequencing. Plaques confirmed of gene transfer were subjected to plaque purification for three times.

The viruses subjected to three times of plaque purification were subjected to small-scale cultivation. The colony obtained after the third purification was suspended in 700 μl of 10% FCS/MEM medium and subjected to ultrasonication in cold water. Following centrifugation (2000 rpm, 10 min), 500 μl of supernatant was added to primary cultured kidney cells seeded in T25 for infection at 30° C. for 2 hours. After the infection, the virus solution was removed by suction and the cells were washed with 2.5 ml of 10% FCS/MEM medium. The medium was removed by suction and 2.5 ml of 10% FCS/MEM medium was newly added for cultivation at 30° C. for 72 hours. After 72 hours, the cells were scraped off from the flask with a scraper to collect the cell suspension. The collected cell suspension was subjected to ultrasonication (30 sec, 4 times) in cold water, followed by centrifugation, and the supernatant was collected as the virus solution. The collected virus solution was serially diluted and then added to RK13 cells or primary cultured kidney cells that had been seeded onto 6-well plates for infection at 30° C. for an hour. The virus solution was removed by suction and the cells were washed twice with PBS(−) and added with 10% FCS/0.5% methylcellulose/MEM medium for cultivation at 30° C. for 72 hours. After 72 hours, the number of plaques formed in the well was counted to calculate the titer.

Based on this calculated titer, mass-scale culture was performed. RK13 cells or primary cultured kidney cells were seeded into ten T175 flasks. Once the cells reached confluence, the recombinant vaccinia virus solution was used for infection at moi=0.1 and at 30° C. for 2 hours. Following infection, the virus solution was removed by suction and the cells were washed with 20 ml of 10% FCS/MEM medium. The medium was removed by suction and 20 ml of 10% FCS/MEM medium was newly added to culture at 30° C. for 72 hours. After 72 hours, the cells were scraped off from the flasks using a scraper, and the cell suspensions were collected and frozen at −80° C. for preservation. This cell suspension was subjected to three rounds of freezing and thawing, followed by ultrasonication (30 seconds, 4 times) in cold water and centrifugation to collect the supernatant as a virus solution. The collected virus solution was transferred to a high-speed centrifugation tube and subjected to centrifugation at 18000 rpm for 45 minutes to allow precipitation of the virus. The supernatant was removed by suction, and then the pellets were resuspended in a small amount of 10% FCS/MEM medium. By this procedure, a virus solution that was concentrated ten times stronger than that with the T175 flask cultivation was prepared. This concentrated virus solution was serially diluted and used to infect RK13 cells or primary cultured kidney cells that had been seeded onto a 6-well plate, and the virus titers of the solutions were calculated in the same manner as the above-described method. The concentrated virus solutions with calculated titers were used in various experiments described in the following examples.

Example 2

Confirmation of HCV Gene Transfer by PCR

Figure 2:
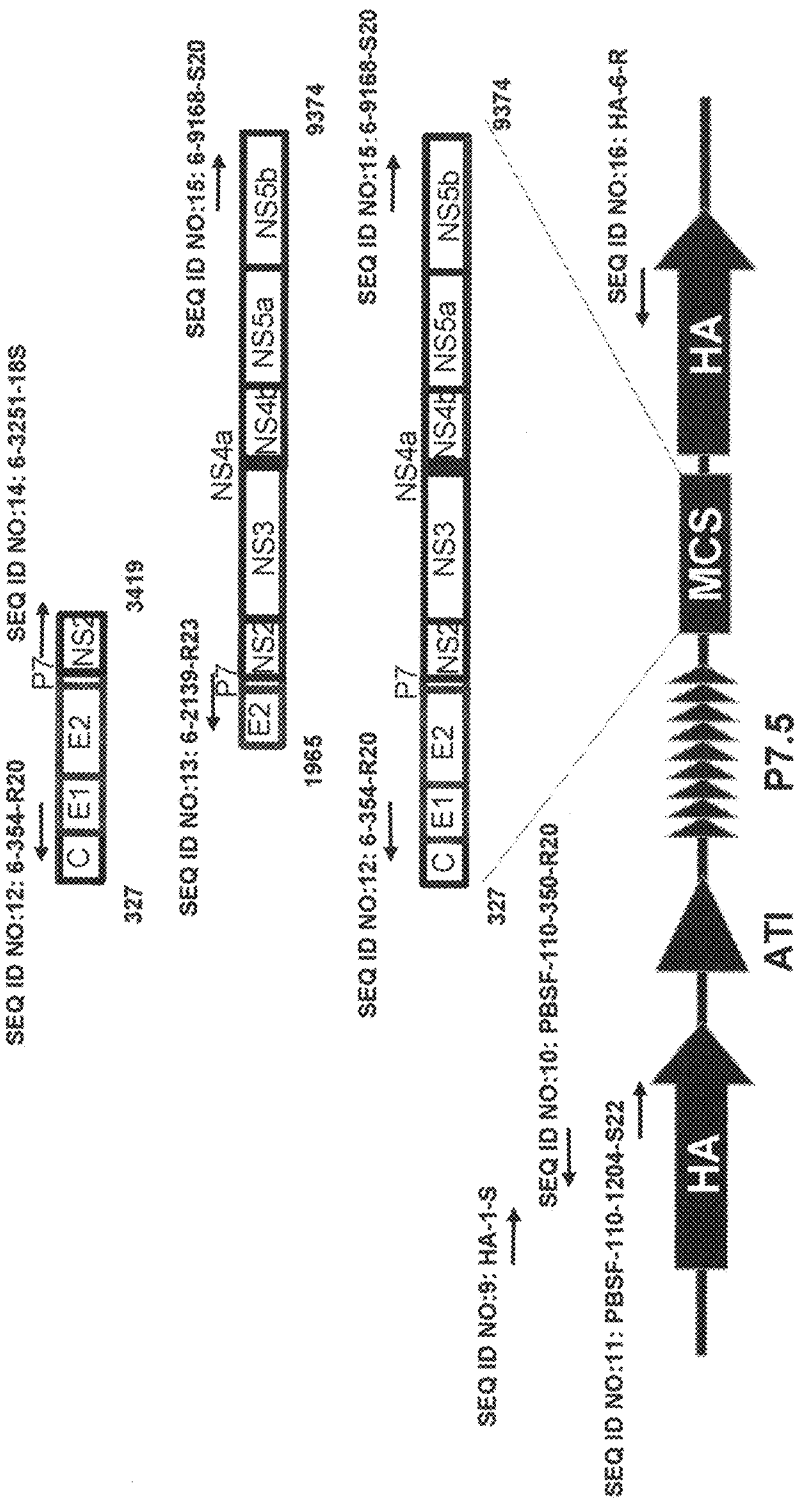
FIG. 2 shows the positions and the names of the primers used for confirming HCV gene transfer by PCR.
Figure 3:
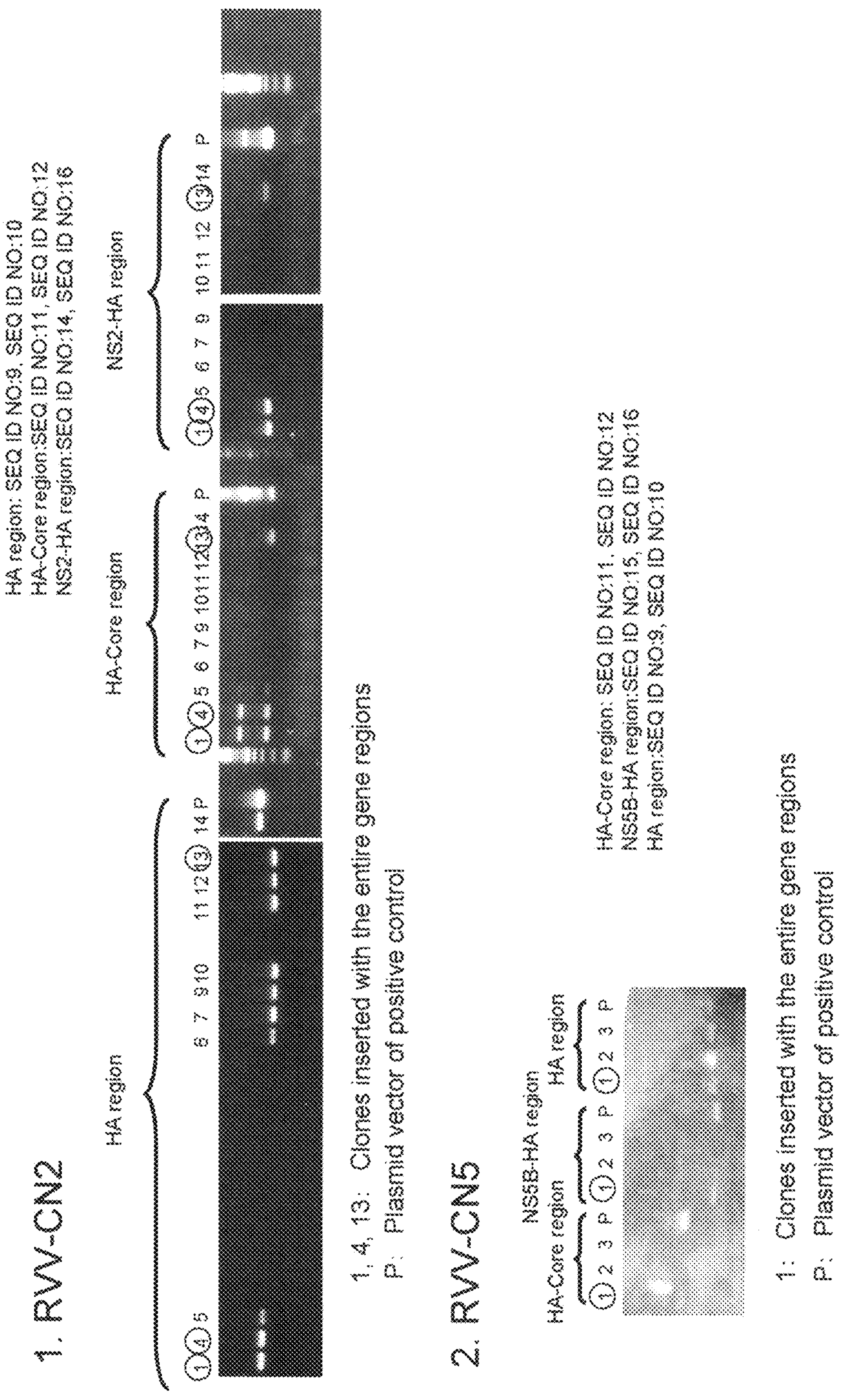
FIG. 3 shows pictures of agarose gel electrophoreses showing the results obtained by confirming HCV gene transfer by PCR.

PCR was performed using the following primers specific to HCV gene and the obtained recombinant vaccinia virus genome as a template to confirm whether or not HCV gene was introduced into the virus genome (FIGS. 2 and 3).

(1) Nucleotide Sequences of Primers for Cloning

```
Fw: HCV-CL-Fw
                                        (SEQ ID NO: 5)
5-GGGCGGCCCTGCAGGTAATACGACTCACTATAGGGCGTAGACCGT
GCATCATGAGCACAAATCCTAAACCCCAAAGAAAAACCAAACG-3

Rv: HCV-CL-MRv
                                        (SEQ ID NO: 6)
5-GGGCGGCGCGATCGCCTATCATTAAAGGAGCCGCCACCCCTGCCCT
TCAAGACTATC-3

Fw: HCV-CL-MFw
                                        (SEQ ID NO: 7)
5-GGGCGGCCCTGCAGGTAATACGACTCACTATAGGGCGTAGACCGT
GCATCATGACGCGGCCGCCGCAAGGCAACTGGTTCGGC-3

Rv: HCV-CL-Rv
                                        (SEQ ID NO: 8)
5-GGGCGGCGCGATCGCCTATCATTATCGGTTGGGGAGCAGGTAGAT
```

GCCTAC-3

(2) Nucleotide Sequences of Primers for PCR for Confirming the Insert

```
<HA>
Fw: HA-1-S
                            (SEQ ID NO: 9)
5-GGTCTTATATACACCGAGTAAGG-3

Rv: PBSF-110-350-R20
                           (SEQ ID NO: 10)
5-TCAGGAAAGACAGCCATAGC-3

<First half region>
Fw: PBSF-110-1204-S22
                           (SEQ ID NO: 11)
5-CATCACATTGAAACATTGGGAC-3

Rv: 6-354-R20
                           (SEQ ID NO: 12)
5-GATTTGTGCTCATGATGCAC-3

Rv: 6-2139-R23
                           (SEQ ID NO: 13)
5-CCGAACCACATTTTGTGTAAGTG-3

<Latter half region>
Fw: 6-3251-18S
                           (SEQ ID NO: 14)
5-AGTAGAGCCCGTTGTCTT-3

Fw: 6-9168-S20
                           (SEQ ID NO: 15)
5-TACCTCTTCAACTGGGCAGT-3

Rv: HA-6-R
                           (SEQ ID NO: 16)
5-CTAGTTCTGAGAAACCAGAGG-3
```

Specifically, the composition of the reaction solution was 1 U DNA polymerase, 0.3 mM dNTP, 1 μM F primer and 1 μM R primer in 50 μL of buffer that comes with a commercially available polymerase. The cycle conditions were 25 cycles of: denaturing at 95° C. for 0.5 minutes; annealing at 58° C. for 0.5 minutes; and elongation at 72° C. for 2 minutes. The resulting PCR product was subjected to electrophoresis using an agarose gel to confirm the band. As a result, if a single band having the length anticipated based on the primer design was observed, HCV gene was considered to be transferred into the recombinant virus genome whereas HCV gene was not transferred if no such band was observed.

As shown in FIG. 3, as a result of 2 wt % agarose gel electrophoresis of the PCR product (amplified fragment), HCV gene was found to be transferred into the recombinant virus genome.

Example 3

Confirmation of HCV Protein Expression by Western Blot Method

The recombinant vaccinia virus RVV-S was used to infect RK13 cells that had been seeded onto a 6-well plate at moi=30 and at 30° C. for 2 hours. After infection, the virus solution was removed by suction and the cells were washed twice with PBS(−). To each well, 2 ml of 10% FCS/MEM medium was added for cultivation at 30° C. for 24 hours. After 24 hours, the medium was removed by suction, and 100 μA of lysis buffer (1% SDS, 0.5% NP-40, 0.15 M NaCl, 10 mM Tris-HCl (pH 7.4)) was added to lyse the cells, and the resultant solution was transferred into a 1.5 ml Eppendorf tube. The collected solution was subjected to ultrasonication in cold water until viscosity became zero. The protein amount in the prepared solution was quantified according to Lowry method.

Electrophoresis was carried out for 50 μg of protein with 10% acrylamide gel. At the end of the electrophoresis, the gel was removed, and the protein in the gel was transferred onto a PVDF membrane with a semi-dry blotter by running a current at 5.5 $mA/cm^2$ for 60 minutes. After washing the membrane with a TBS-T solution, the membrane was immersed into a 5% skimmed milk-TBS-T solution for blocking. After blocking, the membrane was washed for three times with a TBS-T solution. The primary antibody was a mouse monoclonal antibody obtained by purifying Core-31-2, E1-384, E2-544, NS3-10-1, NS4B-52-1 and NS5B-14-5 clone IgG. The protein amount of the purified antibody was quantified by Lowry method and prepared to be 10 μg/ml for use. At the end of the reaction with the primary antibody, the membrane was washed for three times with a TBS-T solution. The secondary antibody used was anti-rabbit IgG-linked HRPO (from Donkey, Amersham). At the end for the reaction with the secondary antibody, the membrane was again washed for three times with a TBS-T solution, and an ECL solution was added to the membrane for film development.

Figure 4:
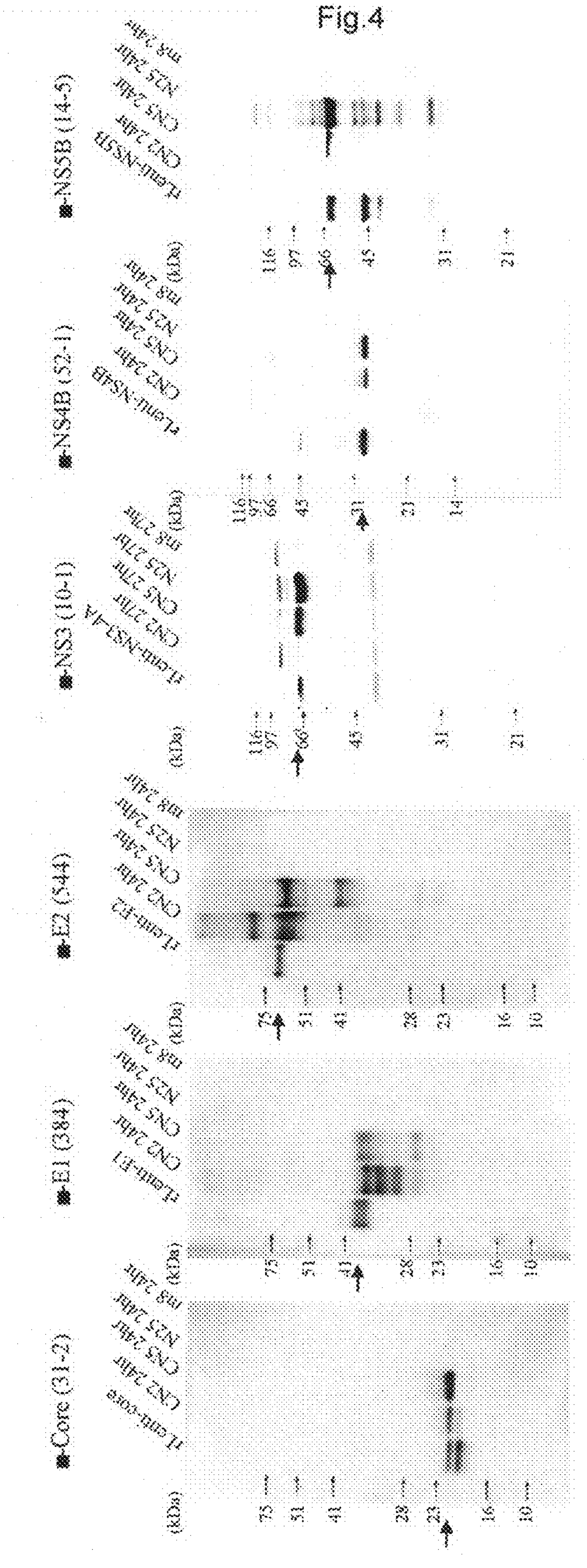
FIG. 4 shows pictures of PVDF membranes showing the results obtained by confirming HCV protein expression by Western blot method.

Consequently, as shown in FIG. 4, HCV protein was found to be expressed in the recombinant virus genomes RVV-CN2, RVV-N25 and RVV-CN5.

Example 4

Figure 5:
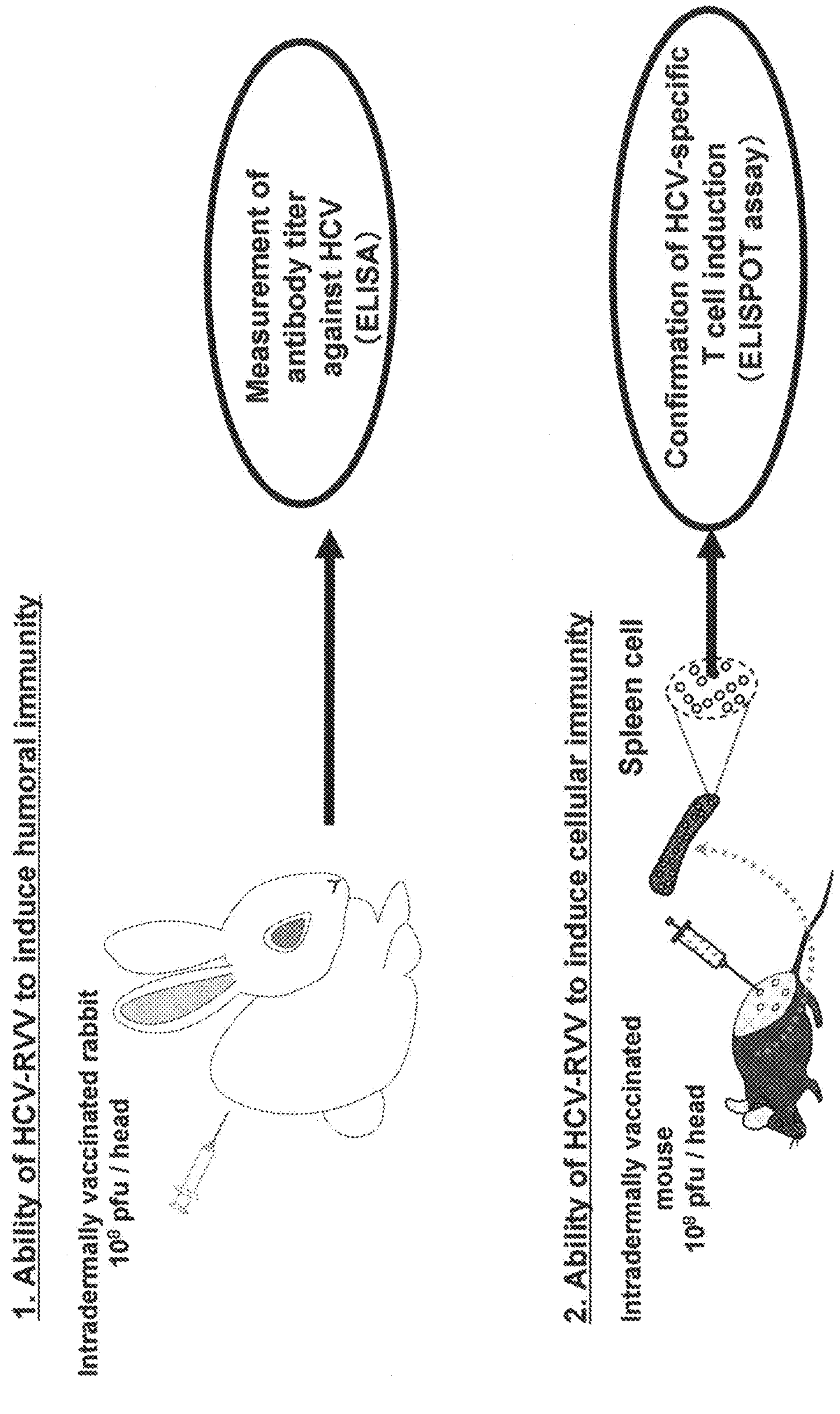
FIG. 5 shows a method for confirming the ability of HCV-RVV to induce humoral/cellular immunity.

Experiments of Vaccination of Rabbits and Mice with Recombinant Vaccinia Viruses (FIG. 5)

FIG. 5 shows a method for confirming the ability of HCV-RVVs to induce humoral/cellular immunity.

New Zealand white female rabbits were transendothelially vaccinated with the recombinant vaccinia viruses or the parent strain LC16m8 obtained in Example 1 at $1\times10^8$ pfu. Blood was drawn from the ear vein after 1, 2, 3, 4 and 6 weeks following the vaccination. Furthermore, after six weeks following the initial viral vaccination, RVV-S was used again for vaccination at $1\times10^8$ pfu. Similarly, blood was again drawn from the ear vein after 1, 2, 3, 4 and 6 weeks following the second vaccination. All of the collected blood was drawn into vacuum blood-collecting tubes (TERUMO, trade name: Venoject II vacuum blood-collecting tubes (sterile), 9 mL), and subjected to centrifugation (3000 rpm, 20 minutes) to separate and collect the sera. The sera were frozen at −20° C. for preservation until the later-described ELISA test.

Example 5

Measurement of Antibody Titers Against HCV Protein in Sera of HCV-RVV-Vaccinated Rabbits by ELISA Method A 96-well plate was coated with core protein and E2 protein, to which a 100-fold dilution of the frozen serum sample was added. After leaving it to stand at room temperature for an hour, the 96-well plate was washed with a TBS-T solution and then anti-rabbit IgG-linked HRPO (from Donkey, Amersham) was added to the 96-well plate as a secondary antibody. After the reaction with the secondary antibody at room temperature for an hour, the 96-well plate was again washed for three times with a TBS-T solution, to which a color development solution was added at 100 μl/well. After leaving it to stand at room temperature for 10-20 minutes, absorbance at 450 nm was measured with a microplate reader.

Figure 6:
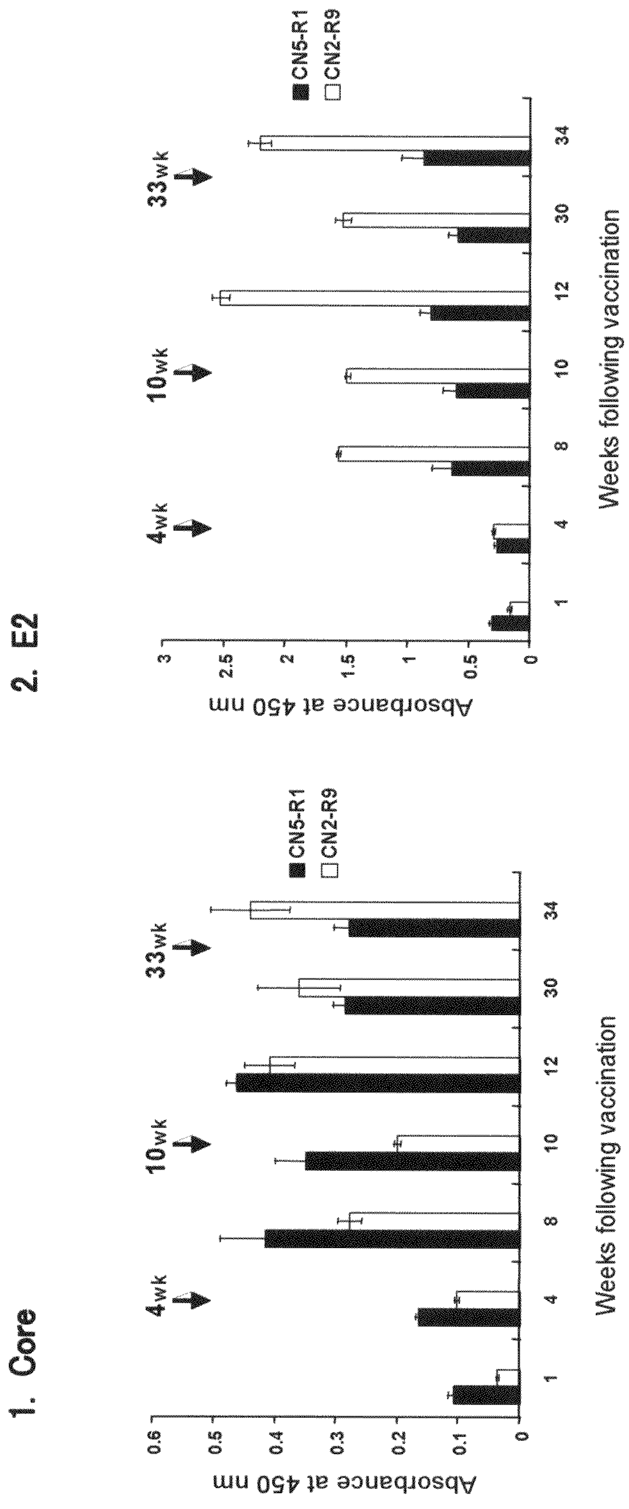
FIG. 6 shows the results obtained by measuring the effect of HCV-RVV as a vaccine by ELISA method with respect to its ability to induce humoral immunity.

As a result, as shown in FIG. 6, higher antibody titers were induced against core and E2 in the sera of RVV-CN2- and RVV-CN5-vaccinated rabbits.

Example 6

Confirmation of Cellular Immunity-Inducing Abilities of HCV-RVVs as Vaccines by ELISPOT Assay (Day 1)

The purified anti-mouse IFN-γ antibody (R4-6A2) (1 μg/ml) (Pharmingen) was seeded onto a 96-well nitrocellulose plate at 75 to 100 μl/well while adjusting the final concentration to be 8 μg/ml (125-fold diluted in sterile PBS) and left to stand at 4° C. overnight.

(Day 2)

Spleen cells were collected from the mouse and allowed to suspend at a suitable amount in washing RPMI. The washing RPMI used was supplemented with 2.5% FCS. The cells were collected by centrifugation at 1200 rpm at 4° C. for 5 minutes. The cells were treated with ACK, suspended in washing RPMI at a suitable amount, and again centrifuged at 1200 rpm and at 4° C. for 5 minutes to collect the cells. 500 μl of washing RPMI followed by the cell suspension were forced to pass through a filter. After complete passage, the cells were washed with 1.5 ml of washing RPMI. The resultant was washed once with 10% FCS-supplemented RPMI, suspended in H-h medium and adjusted to $1\times10^7$/ml.

1) H-h medium: A mixture of equal amounts of 10% FCS-supplemented RPMI and 10% FCS-supplemented CLICK'S medium.

2) 10% FCS-supplemented RPMI: RPMI-1640 (SIGMA R8758), FCS (final 10%), 2-mercaptoethanol (final concentration 5 μM), penicillin-streptomycin (final concentration PCs:100 u/ml, SM:0.1 mg/ml) and 7.5% $NaHCO_3$ 4 ml 3) 10% FCS-supplemented CLICK'S medium: CLICK'S medium (SIGMA C5572), FCS (final concentration 10%), 2-mercaptoethanol (final concentration 5 μM), penicillin-streptomycin (final concentration PCs:100 u/ml, SM:0.1 mg/ml) and 7.5% $NaHCO_3$ 4 ml Initiation of Cultivation The 96-well nitrocellulose plate was washed for three times with PBS (100 μl/well), added with 10% FCS-supplemented RPMI at 100 μl/well, and placed in a $CO_2$ incubator at 37° C. for an hour for blocking. The medium was discarded, and effector cells were seeded in two-fold serial dilution from $1\times10^6$/100 μl/well to $0.125\times10^6$/100 μl/well.

A peptide solution (200 μg/ml) was added at 100 μl/well (final concentration 100 μg/ml) for cultivation in a $CO_2$ incubator at 37° C. for 24 hours.

(Day 3)

The medium was discarded, and the resultant was washed for ten times with PBS, 0.05% Tween 20 (200 μl/well). The biotinated anti-mouse IFN-γ (XMG1.2) (0.5 mg/ml) (Pharmingen) was adjusted to a final concentration of 2 μg/ml (250-fold diluted in PBS) and added at 100 μl/well. The resultant was left to stand at 4° C. overnight.

(Day 4)

The 96-well nitrocellulose plate was washed for ten times with PBS, 0.05% Tween 20 (200 μl/well). Streptavidin-alkaline phosphatase (1 mg/ml) (MABTECH AB) was adjusted to a final concentration of 1 μg/ml (1000-fold diluted in PBS) and added at 100 μl/well.

The resulting solution was left to stand at room temperature for 1.5 hours. A 25×AP color development buffer (BIO-RAD) was 25-fold diluted with DW and 1/100 amounts of color reagents A and B (BIO-RAD) were added to prepare a reaction mixture. The 96-well nitrocellulose plate was washed for ten times with PBS, 0.05% Tween 20 (200 μl/well). The reaction mixture was added at 100 μl/well and left to stand at room temperature for 10-20 minutes. Once color was developed and a dark spot appeared, the reaction mixture was discarded and thoroughly washed in water. The bottom of the 96-well nitrocellulose plate was peeled off and dried to count the number of spots with ELISPOT Reader.

Figure 7:
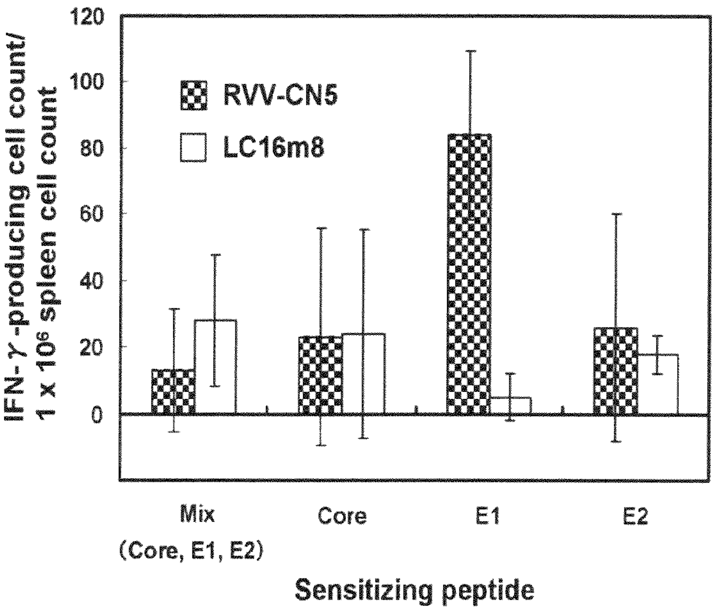
FIG. 7 shows the results obtained by measuring the effect of HCV-RVV as a vaccine by ELISPOT assay with respect to its ability to induce cellular immunity.

The resulting counts are shown in FIG. 7, where strong cellular immunity was induced.

Example 7

Examination of Therapeutic Effect of HCV-RVVs Against Hepatitis C

A transgenic (Cre/loxP/HCV-Tg) mouse (in FIG. 8, "loxP-HCV") transferred with HCV gene with a Cre/loxP system was mated with an IFN-induced Cre-expressing transgenic mouse (in FIG. 8, "MxCre") to prepare a Tg mouse (Cre/loxP/HCV-MxCre Tg) that switchingly expresses HCV gene at an arbitrary time (FIG. 8) for analyzing the pathological condition thereof. For analysis of the pathological condition, poly IC, i.e., an interferon-inducing agent, was used in order to allow gene expression of recombinant enzyme Cre with interferon.

Figure 8:
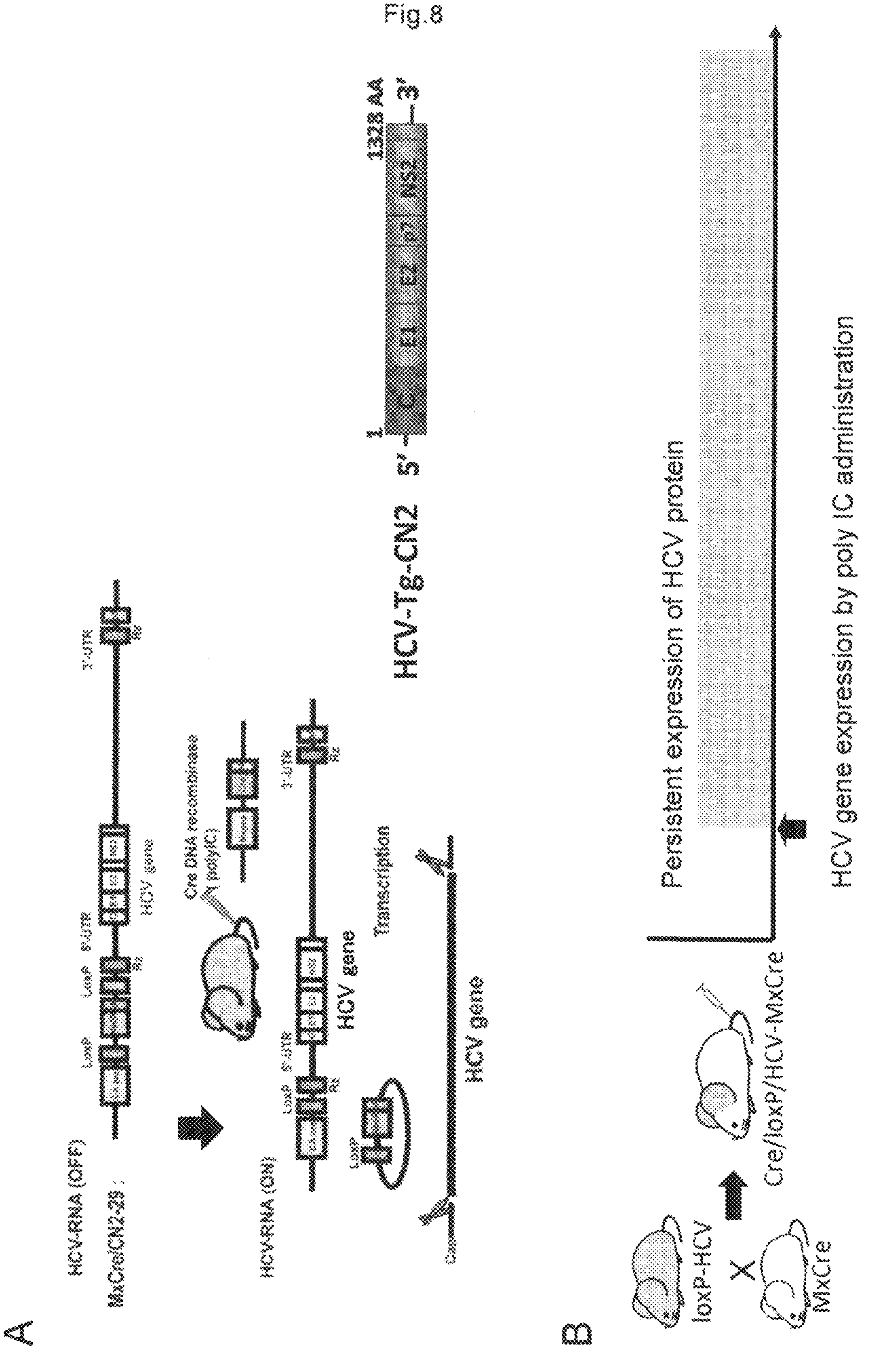
FIG. 8 shows Cre/loxP switching gene expression in a transgenic mouse expressing hepatitis C virus gene.

Here, in FIG. 8, Panel A shows expression of HCV gene by Cre/loxP switching system while Panel B shows mating between the loxP-HCV transgenic mouse and the MxCre gene-expressing transgenic mouse.

Figure 9:
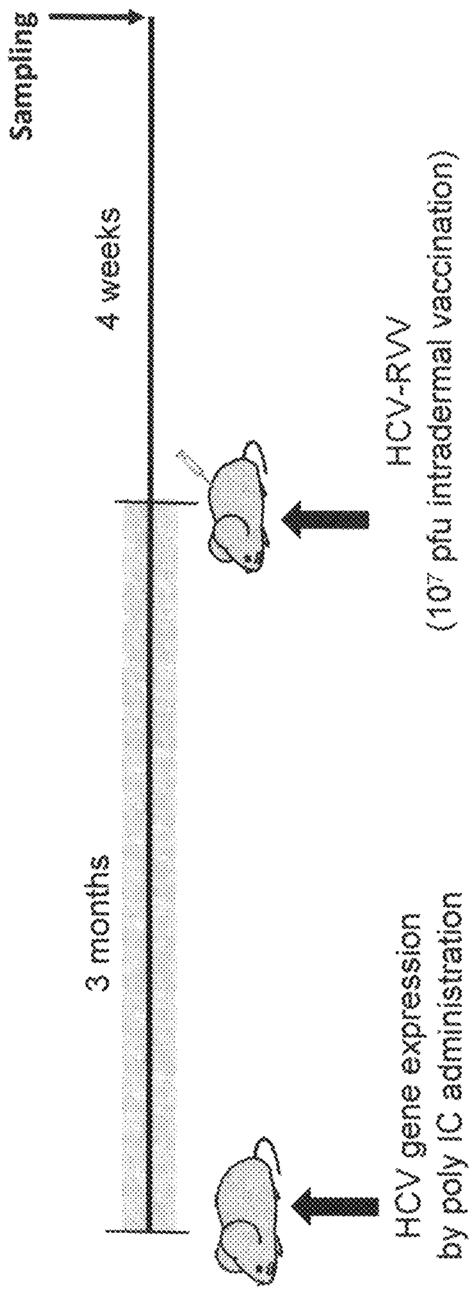
FIG. 9 shows daily changes in the amount of HCV core protein in the liver of the transgenic mouse after the HCV gene expression (Panel A) and tissue alteration in the liver of the transgenic mouse due to onset of hepatitis (Panel B).

As HCV-RVVs, RVV-CN2 that predominantly expresses the structural protein of HCV, RVV-N25 that expresses the replication-associated nonstructural protein, and RVV-CN5 that expresses the whole protein were used (FIG. 1). In order to assess the therapeutic effects of these HCV-RVVs, Cre/loxP/HCV-MxCre Tg mice that persistently expressed HCV protein for 3 months were intradermally vaccinated once with the HCV-RVVs ($1\times10^7$ pfu), and the mouse livers were sampled after four weeks following the vaccination (FIG. 9). Subsequently, expression levels and morphology of HCV proteins in the mouse livers were examined.

Figure 10:
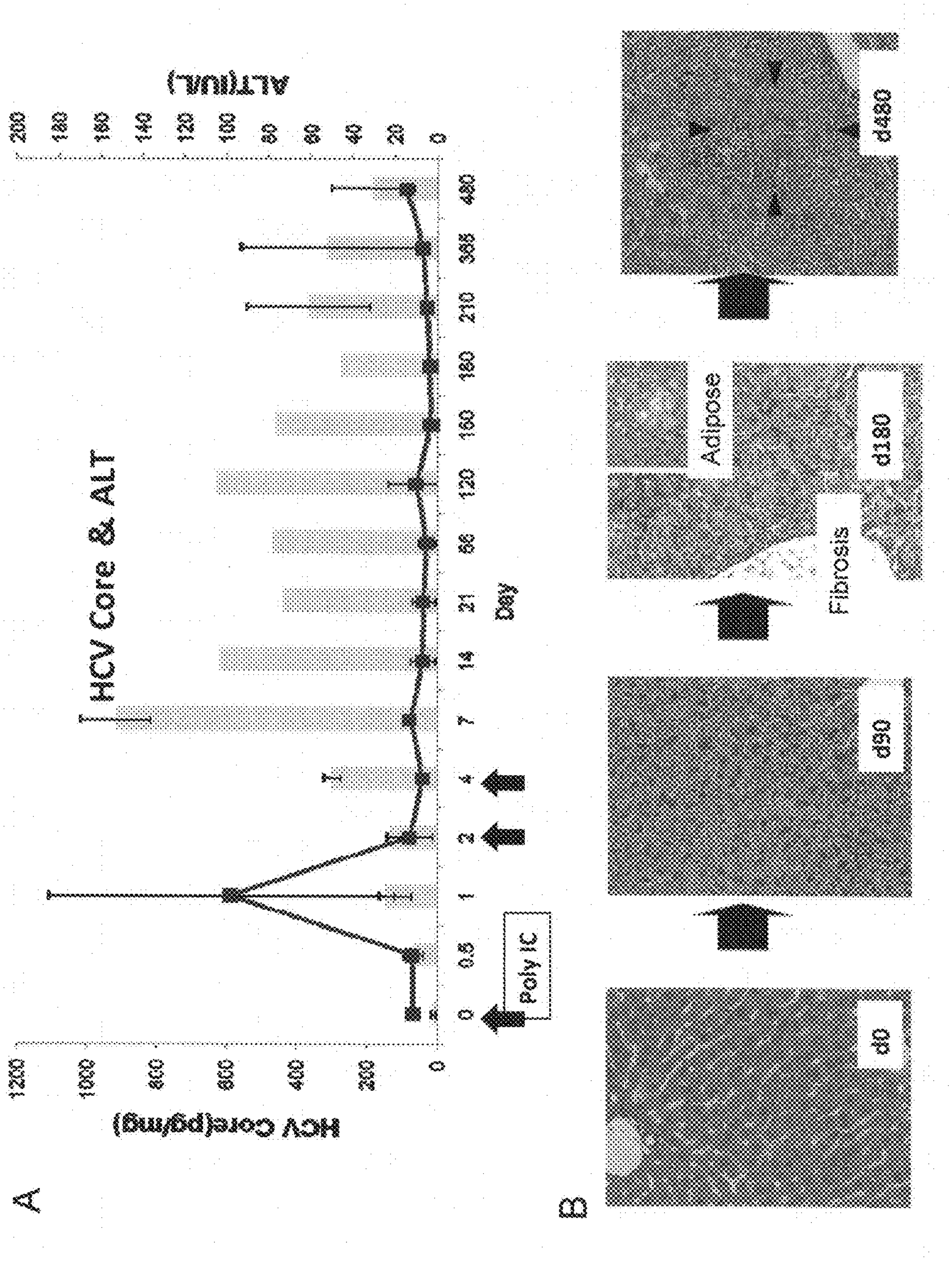
FIG. 10 shows administration schedule of the HCV recombinant vaccinia virus to the HCV transgenic mice

The results are shown in FIG. 10. In FIG. 10, Panel A shows the transitions of HCV core protein amount ("HCV core") and ALT (alanine aminotransferase), in which the HCV core protein amount ("HCV core") and ALT are represented by a bar graph and a line graph, respectively. ALT is an indicator of the degree of liver damage. In Panel B, "d0", "d90", "d180" and "d480" indicate tissue alteration in the liver before the HCV gene expression, and after 90 days, 180 days and 480 days following the HCV gene expression, respectively.

The HCV protein in the liver of the Cre/loxP/HCV-MxCre Tg mouse (in FIG. 10, "HCV core") was not completely eliminated and persistent expression was confirmed for more than a year, indicating a pathological condition of chronic hepatitis such as inflammation or adipose degeneration, fibrosis and the like in the liver (FIG. 10).

Figure 11:
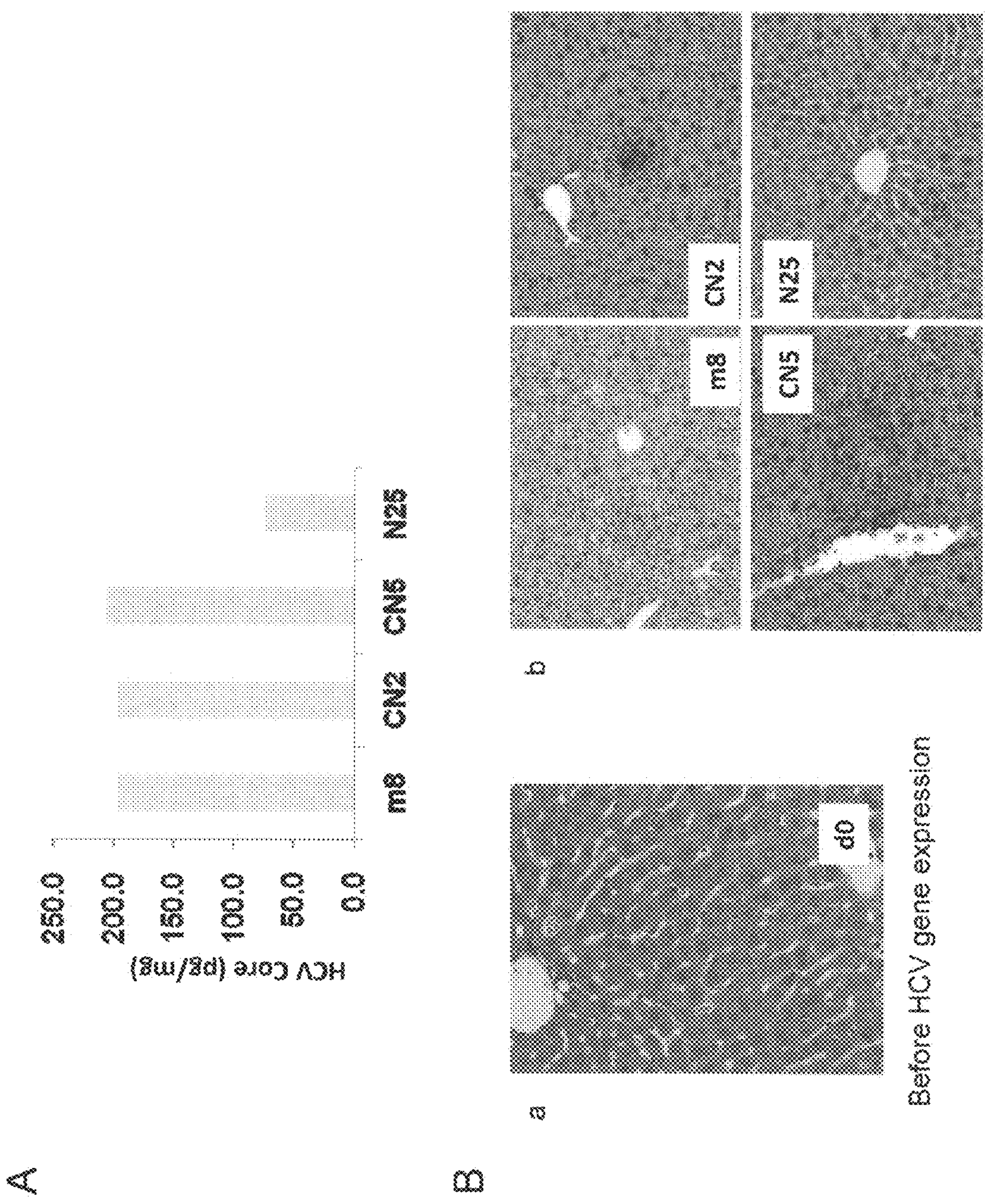
FIG. 11 shows the therapeutic effect after the administration of the HCV recombinant vaccinia virus to the HCV transgenic mice.

Furthermore, in the livers of the Cre/loxP/HCV-MxCre Tg mice after four weeks following the HCV-RVV vaccination, the expression level of the core protein was decreased for the RVV-N25 vaccination group (FIG. 11). Moreover, for the RVV-N25 group, morphological abnormality in the liver (cord-like structure of the liver, conditions of the liver cells or the like) returned to normal (FIG. 11).

In FIG. 11, "m8", "CN2", "CN5" and "N25" represent LC16m8 strain, RVV-CN2, RVV-CN5 and RVV-N25, respectively. Panel A shows the amounts of HCV core proteins in the livers while Panel B shows images of the liver tissues after four weeks following the HCV-RVV vaccination. In Panel B, "a" shows the image of the liver tissue prior to the HCV gene expression while "b" shows the images of the liver tissues after four weeks following the HCV-RVV vaccination. As can be appreciated from FIG. 11, the liver of the mouse administered with RVV-N25 returned to normal. Thus, the vaccinia virus of the present invention was shown to have a therapeutic effect on hepatitis C.

INDUSTRIAL APPLICABILITY

According to the present invention, there are provided a novel recombinant vaccinia virus that is efficacious and highly safe in preventing or treating hepatitis C, and a prophylactic or therapeutic agent for hepatitis C (a vaccine for preventing or treating hepatitis C) comprising the novel virus.

SEQUENCE LISTING

SEQ ID NO:5: Synthetic DNA
SEQ ID NO:6: Synthetic DNA
SEQ ID NO:7: Synthetic DNA
SEQ ID NO:8: Synthetic DNA
SEQ ID NO:9: Synthetic DNA
SEQ ID NO:10: Synthetic DNA
SEQ ID NO:11: Synthetic DNA
SEQ ID NO:12: Synthetic DNA
SEQ ID NO:13: Synthetic DNA
SEQ ID NO:14: Synthetic DNA
SEQ ID NO:15: Synthetic DNA
SEQ ID NO:16: Synthetic DNA
SEQ ID NO:17: Synthetic peptide
SEQ ID NO:18: Synthetic peptide
SEQ ID NO:19: Synthetic peptide
SEQ ID NO:20: Synthetic peptide

The invention claimed is:

1. A recombinant vaccinia virus comprising an expression promoter and a DNA of (a) or (b) below: (a) DNA consisting of the nucleotide sequence of SEQ ID NO:2; or (b) DNA that hybridizes with DNA consisting of a nucleotide sequence complementary to the nucleotide sequence of SEQ ID NO:2, that has 90% or more homology with the nucleotide sequence of SEQ ID NO:2, and that codes for a nonstructural protein and a structural protein of hepatitis C virus.

2. The recombinant vaccinia virus according to claim 1, wherein the vaccinia virus is LC16m8 strain.

3. The recombinant vaccinia virus according to claim 1, wherein the expression promoter is a hybrid promoter.

4. The recombinant vaccinia virus according to claim 3, wherein the nucleotide sequence of the hybrid promoter is DNA consisting of the nucleotide sequence of SEQ ID NO:4.

5. An immunogenic composition comprising the recombinant vaccinia virus according to claim 1.

* * * * *

SEQUENCE LISTING

<160> NUMBER OF SEQ ID NOS: 20

<210> SEQ ID NO 1
<211> LENGTH: 3093
<212> TYPE: DNA
<213> ORGANISM: Hepatitis C virus

<400> SEQUENCE: 1

```
cgtagaccgt gcatcatgag cacaaatcct aaaccccaaa gaaaaaccaa acgtaacacc      60

aaccgccgcc cacaggacgt caagttcccg ggtggtggtc agatcgttgg tggagtttac     120

ctgttgccgc gcaggggccc caggttgggt gtgcgcgcga ctaggaagac ttccgagcgg     180

tcacaacctc gtggaaggcg acaacctatc cccaaggctc gccagcccga gggcagggcc     240

tgggctcagc ccgggtaccc ttggcccctc tatggcaacg agggcatggg gtgggcagga     300

tggctcctgt caccccgcgg ctcccggcct agttggggcc ccacggaccc ccggcgtagg     360

tcgcgtaatt tgggtaaggt catcgatacc ctcacatgcg gcttcgccga cctcatgggg     420

tacattccgc tcgtcggcgc ccccctaggg ggcgttgcca gggccctggc acatggtgtc     480

cgggttgtgg aggacggcgt gaactatgca acagggaatt tgcccggttg ctctttctct     540

atcttcctct tggctctgct gtcctgtttg accatcccag cttccgctta tgaggtgcgc     600

aacgtatccg ggatatacca tgtcacgaac gactgctcca actcaagtat tgtgtatgag     660

gcagcggaca tgatcatgca tacccccggg tgcgtgccct gcgttcggga gggcaactcc     720

tcccgttgct gggtggcact tactcccacg ctagcggcca ggaatgccag cgtccccact     780

acggcaatac gacgccatgt cgatttgctc gttggggcgg ctgctttctg ctccgctatg     840
```

-continued

```
tatgtgggag atctctgcgg atctgttttc cttgtctccc agctgttcac cttctcgccc    900
cgccggcatg agacaataca ggactgcaat tgctcaatct atcccggcca cgtgtcaggt    960
caccgcatgg cttgggacat gatgatgaac tggtcgccta caacggccct ggtggtgtcg   1020
cagttactcc ggatcccaca agctatcgtg gacatggtgg cgggggctca ctggggtgtc   1080
ctagcgggcc ttgcctacta ttccatggtg gggaactggg ctaaggtatt gattgtgatg   1140
ctactttttg ccggcgtcga cggggagacc cgtgtgacag gggggcagat agccagaaat   1200
gcctactcgc tcacgaccct cttttcatct gggtcggctc agaacatcca gctcataaac   1260
accaacggta gctggcacat caacaggact gccctgaact gcaatgactc cctcaacacc   1320
gggtttcttg ccgcgctgtt ctacacgcac aagttcaacg cgtccggatg tccagagcgc   1380
ttggccagct gccgccccat tgacaagttc gatcaggggt ggggtcccat cacttatgct   1440
gagcagggcg gccaggacca gaggccttat tgctggcact acgcacctaa accatgtggt   1500
attgtatccg cgtcgaaggt gtgtggtcca gtgtattgtt tcaccccaag cccagttgta   1560
gtggggacga ccgatcggtt cggtgtccct acgtatagct gggggggagaa tgagacagac   1620
gtgctgctcc ttaacaacac gcggccgccg caaggcaact ggttcggctg tacgtggatg   1680
aacggcactg ggttcaccaa gacatgcggg ggcccccgt gtaacatcgg ggggggcggc    1740
aataacacct tgacctgccc tacggactgt ttccggaagc accccgcggc cacttacaca   1800
aaatgtggtt cgggaccttg gctgacaccc aggtgcttgg tagactaccc atacaggctc   1860
tggcactacc cctgcactgc caactttacc atcttcaagg ttaggatgta tgtagggggc   1920
gtggagcaca ggctcgatgc tgcatgcaat tggacccgag gggaacgttg caacttggag   1980
gatagggata gattggagct cagcccgcta ctgctgtcta caacagagtg gcaggtgctg   2040
ccctgttctt tcaccaccct accggctctg tccactggtt taattcatct ccatcagaac   2100
atcgtggacg tgcaatacct gtacggtata gggtcggcag ttgtttcctt tgcaatcaaa   2160
tgggactata tcgtgatact tttcctcctc ctggcggacg cgcgcgtctg tgcctgcttg   2220
tggatgatgc tgctgatagc ccaggccgag gccgccttag aaaacctggt ggtcctcaat   2280
gcggcgtccg tggccggagc gcatggcatt ctctccttcc ttgtgttctt ctgtgccgcc   2340
tggtacatca agggcaagct ggtccccggg gcagcatatg ctttctatgg agtatggccg   2400
ctgctcctgc ttctgctggc cttaccacca cgagcttacg ctatggagcg ggagatggct   2460
gcatcgtgcg gaggcgcggt gtttgtaggt ctggtactct tgactttgtc accatactat   2520
aaagagttcc tcgccaggct catatggtgg ttgcaatatt ttatcaccag agccgaggcg   2580
cacctgcaag tgtggatccc ccccctcaac attcgggggg gccgcgatgc catcatcctc   2640
ctcgcgtgtg tagtccaccc agagctaatc tttgacatca ccaaactcct gctcgccata   2700
ctcggtccgc tcatggtgct ccaggctagc ataactcaag tgccgtactt cgtacgcgcc   2760
caagggctca ttcgtgcatg catgttggtg cggaaggtag ccgggggcca ttatgtccaa   2820
atggcctttg tgaagctgac cgcactgaca ggtacgtacg tttatgacca tctaactcca   2880
ctgcgggact gggcccacgc gggcctgcga gacctcgcgg tggcagtaga gcccgttgtc   2940
ttctctgaca tggagaccaa ggtcatcacc tggggggcag acaccgcagc gtgtggggac   3000
attatcttgg gtctacctgt ctccgcccga aggggtaggg agatacttct ggggccggcc   3060
gatagtcttg aagggcaggg gtggcggctc ctt                                3093
```

<210> SEQ ID NO 2
<211> LENGTH: 7410

<212> TYPE: DNA
<213> ORGANISM: Hepatitis C virus

<400> SEQUENCE: 2
acgcggccgc cgcaaggcaa ctggttcggc tgtacgtgga tgaacggcac tgggttcacc 60
aagacatgcg ggggcccccc gtgtaacatc gggggggcg gcaataacac cttgacctgc 120
cctacggact gtttccggaa gcaccccgcg gccacttaca caaaatgtgg ttcgggacct 180
tggctgacac ccaggtgctt ggtagactac ccatacaggc tctggcacta cccctgcact 240
gccaacttta ccatcttcaa ggttaggatg tatgtagggg gcgtggagca caggctcgat 300
gctgcatgca attggacccg aggggaacgt tgcaacttgg aggataggga tagattggag 360
ctcagcccgc tactgctgtc tacaacagag tggcaggtgc tgccctgttc tttcaccacc 420
ctaccggctc tgtccactgg tttaattcat ctccatcaga acatcgtgga cgtgcaatac 480
ctgtacggta tagggtcggc agttgtttcc tttgcaatca aatgggacta tatcgtgata 540
cttttcctcc tcctggcgga cgcgcgcgtc tgtgcctgct tgtggatgat gctgctgata 600
gcccaggccg aggccgcctt agaaaacctg gtggtcctca atgcggcgtc cgtggccgga 660
gcgcatggca ttctctcctt ccttgtgttc ttctgtgccg cctggtacat caagggcaag 720
ctggtccccg gggcagcata tgctttctat ggagtatggc cgctgctcct gcttctgctg 780
gccttaccac cacgagctta cgctatggag cgggagatgg ctgcatcgtg cggaggcgcg 840
gtgtttgtag gtctggtact cttgactttg tcaccatact ataaagagtt cctcgccagg 900
ctcatatggt ggttgcaata ttttatcacc agagccgagg cgcacctgca agtgtggatc 960 cccccctca acattcgggg gggccgcgat gccatcatcc tcctcgcgtg tgtagtccac 1020
ccagagctaa tctttgacat caccaaactc ctgctcgcca tactcggtcc gctcatggtg 1080
ctccaggcta gcataactca agtgccgtac ttcgtacgcg cccaagggct cattcgtgca 1140
tgcatgttgg tgcggaaggt agccgggggc cattatgtcc aaatggcctt tgtgaagctg 1200
accgcactga caggtacgta cgtttatgac catctaactc cactgcggga ctgggcccac 1260
gcgggcctgc gagacctcgc ggtggcagta gagcccgttg tcttctctga catggagacc 1320
aaggtcatca cctgggggc agacaccgca gcgtgtgggg acattatctt gggtctacct 1380
gtctccgccc gaaggggtag ggagatactt ctggggccgg ccgatagtct tgaagggcag 1440
gggtggcggc tccttgctcc catcacggcc tattcccaac agacgcgggg cctacttggt 1500
tgcatcatca ctagcctcac aggccgggac aaaaaccaag tcgaggggga ggttcaagtg 1560
gtctccaccg cgacacaatc cttcctggcg acctgcgtca atggcgcgtg ctggactgtc 1620
ttccatggtg ccggctcaaa gaccttagct ggcccaaaag gtccaatcac ccagatgtac 1680
actaatgtag acctggacct cgtcggctgg caggcgcccc ccgggtcgcg ttctctgaca 1740
ccatgcacct gcggcagctc agacctctat ttggtcacga gacatgctga tgtcattccg 1800
gtgcgccggc ggggcgacag taggggaagc ctactctctc ccagacctgt ctcctacttg 1860
aaaggctcct cgggtggtcc gctgctctgc ccttcgaggc acgctgtggg catcttccgg 1920
gctgctgtgt gcacccgggg ggttgcgaag gcggtggatt tcatacccgt tgaatcaatg 1980
gaaactacta tgcggtctcc ggtcttcacg gataactcat cccccccggc cgtaccgcag 2040
acattccaag tggcccatct acacgcccct actggcagcg gcaagagcac taaggtgccg 2100
gctgcatatg cagcccaagg gtataaggtg ctcgtcctga acccgtccgt tgccgctacc 2160
ttgggttttg ggcgtatat gtctaaggca catggtatcg accccaacat cagaactggg 2220
gtaagggcca tcaccacggg cgcccctatt acatactcca cctacggcaa gttccttgcc 2280
gacggcggtt gttccggggg cgcctatgac atcataatat gtgatgagtg ccactcaact 2340
gactcgacta ccatcttggg cattggcaca gtcctggacc aagcggagac ggctggagcg 2400
cggctcgtcg tgctcgccac cgctacgcct ccgggatcgg tcaccgtgcc acaccccaat 2460
attgaggagg tggccctgtc caacgctgga gaaatcccct tctacggcaa agccatcccc 2520
attgaggtca tcaagggggg aagacatctc attttctgcc attccaagaa gaagtatgac 2580
gagctcgccg caaagctatc agccctcgga cttaatgctg tagcatatta tcggggtctt 2640
gatgtgtccg tcataccgac caacggagac gtcgttgtcg tggcaacaga cgctctaatg 2700
acgggcttta ccggcgactt tgactcagtg atcgactgta acacatgtgt cacccagaca 2760
gtcgatttca gcctggatcc caccttcacc atcgagacga cgaccgtgcc ccaagacgca 2820
gtggcgcgat cacagcggcg gggtaggact ggtaggggca ggagaggcat ctacaggttt 2880
gtgactccag gagaacggcc ctcgggcatg ttcgattcct cggtcctgtg tgagtgctat 2940
gacgcgggct gtgcttggta cgagctcacg cctgctgaga cctcggttag gttgcgggct 3000
tacctgaata caccagggtt gcccgtctgc caggaccatc tggagttttg ggagagcgtc 3060
tccacaggcc tcacccacat agatgcccat tttctgtccc agactaaaca ggcaggagac 3120
aacttcccct acctggtagc ataccaagcc acagtgtgcg ccagagctca agctccacct 3180
ccatcatggg atcaaatgtg gaagtgtctc atacggctca aacccacgct gcacgggcca 3240
acacccctgc tgtataggct aggagccgtc caaaatgaga tcaccctcac acaccccatg 3300
accaaattca tcatggcatg catgtcggct gacctggagg tcgtcactag cacctgggtg 3360
ctagtaggcg gagtccttgc agctctggct gcatattgct tgacaacagg cagtgtggtc 3420
attgtgggta ggatcatctt gtccgggagg ccggctgtta ttcccgacag ggaagtcctc 3480
taccgggagt tcgatgagat ggaagagtgc gcctcacacc tcccttacat cgaacaggga 3540
atgcagcttg ccgagcaatt caagcagaag gcgctcggat tgctgcaaac agccaccaag 3600
caagcggagg ctgctgctcc cgtggtagaa tccaagtggc gagcccttga gaccttctgg 3660
gcgaagcaca tgtggaattt catcagcggg atacagtacc tagcaggctt gtccactctg 3720
cctgggaacc ccgcgatagc atcactgatg gcattcacag cctctatcac cagcccgctc 3780
tccacccaga ataccctatt atttaacatc tggggggggat gggtggctgc ccaactcgcc 3840
ccccccagtg ctgcttcggc tttcgtgggc gccggtatcg ccggtgcggc tgtcggcagc 3900
ataggtcttg ggaaggtgct tgtggacatc ttggcgggat atggggcagg ggtggctggc 3960
gcgctcgtag cttttaagat catgagcggc gaggtgccct ccaccgagga cctggttaac 4020
ttactccctg ccatcctctc tcccggcgcc ctagtcgtcg gggtcgtgtg cgcagcaata 4080
ctgcgtcggc acgtgggccc gggagagggg gctgtacagt ggatgaaccg gctgatagcg 4140
ttcgcctcgc ggggtaacca cgtttccccc gcgcactatg tgcctgagag cgacgctgcg 4200
gcgcgtgtta ctcagatcct ctccggcctt accatcactc agctgctgaa gaggcttcac 4260
cactggatca atgaggactg ctccacgcca tgctccggtt cgtggctaag ggatgtttgg 4320
gactggatat gcacggtgtt gactgacttc aagacctggc tccagtccaa gctcctgccg 4380
cggttaccgg gggtcccttt cttctcgtgt caacgcgggt acaagggagt ctggcggggg 4440
gacggtatca tgcagaccac ctgcccgtgt ggagcacaga tcaccggaca tgtcaaaaac 4500
ggttccatga ggatcgtcgg gcctaaaacc tgcagcagca cgtggcatgg aacgttcccc 4560
atcaacgcat acaccacagg cccatgcgca ccctccccgg cgccaaacta ttccagggcg 4620

-continued

```
ctatggcggg tggccgctga ggagtacgtg gaggttacgc gggtggggga tttccactac   4680
gtgacgggca tgaccactga caacgtaaag tgcccatgcc aggttccggc ccctgaattc   4740
ttcactgagg tggatggagt gcggttgcac aggtacgctc cggcgtgcaa acccctccta   4800
cgggaggagg tcacattcca ggttgggctc aaccaatacc tggttgggtc acagctccca   4860
tgcgagcccg aaccggatgt agcagtgcta acttccatgc ttaccgaccc ctcccacatc   4920
acagcagaga cggcaaagcg taggctggct aggggtctc cccctcctt ggccagttct   4980
tcagctagcc agttatctgc gccttccttg aaggcgacat gcactaccca tcatgactcc   5040
ccggacgttg acctcatcga ggccaacctc ctgtggcggc aggagatggg cgggaacatc   5100
acccgcgtgg agtcagagaa taaggtagta attttggact ctttcgatcc gctccgagcg   5160
gaggaggacg agagggaacc atccgttgcg gcggagatct tgcggaaaac caagaggttc   5220
cccccggcga tgcccatatg ggcacgcccg gattacaacc ctccgttgct agagtcctgg   5280
aaagacccgg actacgtccc tccggtggta cacgggtgcc cgctaccacc taccaaagct   5340
cctccgatac cacccccacg gagaaagagg acggtagtcc tgacagagtc cactgtgtct   5400
tctgccttgg cggagcttgc tactaagacc tttggcagct ccgggtcgtc ggccgtcgac   5460
agcggcacgg caactgctcc tcccgaccag gcttccgacg acggcgacca aggatctgac   5520
gttgagtcgt attcctccat gcccccctctt gagggagagc cgggggaccc cgatctcagc   5580
gacgggtctt ggtctaccgt gagcgaggag gccggtgagg acgtcatctg ctgctcaatg   5640
tcctacacat ggacaggcgc cttgatcacg ccatgcgccg cggaggaaag caagttgccc   5700
atcaacccgt tgagcaactc tttgttgcgt caccacaaca tggtctatgc tacaacatcc   5760
cgcagcgcag gcctacggca gaagaaggtc acctttgaca gactgcaagt cctggacgac   5820
cactaccggg acgtgctcaa ggagatgaag gcgaaggcgt ccacagttaa ggctaaactc   5880
ctatccatag aagaagcctg taagctgacg cccccacatt cggccagatc caaatttggc   5940
tatggggcaa aggacgtccg gaacctatcc agcaaggccg ttaaccacat ccgctccgtg   6000
tggaaggact tgctggaaga cactgagaca ccaattgaca ccaccgtcat ggcaaaaagt   6060
gaggttttct gcgtccaacc agagaaagga ggccgcaagc cagctcgcct tatcgtattc   6120
ccagacttgg gggttcgtgt atgcgagaag atggcccttt atgacgtggt ctccaccctt   6180
cctcaggccg tgatgggctc ctcatacgga ttccagtact cccctggaca gcgggtcgag   6240
ttcctggtga atgcctggaa atcaaagaaa tgccctatgg gcttttcata tgacacccgc   6300
tgttttgact cgacagtcac tgagagtgac atccgtgttg aggagtcaat ttaccaatgt   6360
tgtgacttgg cccccgaagc cagacaggcc ataaagtcgc tcacagagcg gctttacatt   6420
gggggtcccc tgaccaattc aaaagggcag aactgtggct atcgccggtg ccgcgcgagt   6480
ggcgtgctga cgaccagctg cggtaatacc cttacatgtt acttgaaggc ctctgcagcc   6540
tgtcgagctg caaagctccg ggactgcacg atgctcgtga acggagacga cctcgtcgtc   6600
atctgtgaga gtgcgggaac ccaagaggat gaggcgaacc tacgagtctt cacggaggct   6660
atgactaggt attctgcccc ccccggggac ccgccccgac cagaatacga cttggagcta   6720
ataacatcat gttcctccaa tgtgtcggtc gcgcacgatg catctggcaa aagggtatac   6780
tacctcaccc gcgacccctc cacccccctt gcacgggctg cgtgggagac agctagacac   6840
actccagtta attcctggct aggcaacatc attatgtatg cgcccacctt atgggcaagg   6900
atgattctga tgacccattt cttctccatc cttctagccc aggagcaact tgaaaaagcc   6960
```

-continued

```
ctggattgcc agatctacgg ggcctgttac tccattgagc cacttgacct acctcagatc   7020

attgaacgac tccatggtct tagcgcattt tcactccata gttactctcc aggtgagatc   7080

aatagggtgg cttcatgcct caggaaactt ggggtaccac ccttgcgagt ctggagacat   7140

cgggccagaa gtgtccgcgc taagctgctg tcccaggggg ggagggctgc cacttgtggt   7200

aagtacctct tcaactgggc agtaaggacc aagctcaaac tcactccaat cccggcagcg   7260

tcccagttgg acttgtccag ctggttcgtg gctggttaca gcgggggaga catatatcac   7320

agcctgtctc gtgcccgacc ccgctggttc atgttgtgcc tactcctact ttcagtaggg   7380

gtaggcatct acctgctccc caaccgataa                                    7410


<210> SEQ ID NO 3
<211> LENGTH: 9048
<212> TYPE: DNA
<213> ORGANISM: Hepatitis C virus

<400> SEQUENCE: 3

cgtagaccgt gcatcatgag cacaaatcct aaaccccaaa gaaaaaccaa acgtaacacc     60

aaccgccgcc cacaggacgt caagttcccg ggtggtggtc agatcgttgg tggagtttac    120

ctgttgccgc gcaggggccc caggttgggt gtgcgcgcga ctaggaagac ttccgagcgg    180

tcacaacctc gtggaaggcg acaacctatc cccaaggctc gccagcccga gggcagggcc    240

tgggctcagc ccgggtaccc ttggcccctc tatggcaacg agggcatggg gtgggcagga    300

tggctcctgt caccccgcgg ctcccggcct agttggggcc ccacggaccc ccggcgtagg    360

tcgcgtaatt tgggtaaggt catcgatacc ctcacatgcg gcttcgccga cctcatgggg    420

tacattccgc tcgtcggcgc ccccctaggg ggcgttgcca gggccctggc acatggtgtc    480

cgggttgtgg aggacggcgt gaactatgca acagggaatt tgcccggttg ctctttctct    540

atcttcctct tggctctgct gtcctgtttg accatcccag cttccgctta tgaggtgcgc    600

aacgtatccg ggatatacca tgtcacgaac gactgctcca actcaagtat tgtgtatgag    660

gcagcggaca tgatcatgca tacccccggg tgcgtgccct gcgttcggga gggcaactcc    720

tcccgttgct gggtggcact tactcccacg ctagcggcca ggaatgccag cgtccccact    780

acggcaatac gacgccatgt cgatttgctc gttggggcgg ctgctttctg ctccgctatg    840

tatgtgggag atctctgcgg atctgttttc cttgtctccc agctgttcac cttctcgccc    900

cgccggcatg agacaataca ggactgcaat tgctcaatct atcccggcca cgtgtcaggt    960

caccgcatgg cttgggacat gatgatgaac tggtcgccta caacggccct ggtggtgtcg   1020

cagttactcc ggatcccaca agctatcgtg gacatggtgg cgggggctca ctggggtgtc   1080

ctagcgggcc ttgcctacta ttccatggtg gggaactggg ctaaggtatt gattgtgatg   1140

ctactttttg ccggcgtcga cggggagacc cgtgtgacag gggggcagat agccagaaat   1200

gcctactcgc tcacgaccct cttttcatct gggtcggctc agaacatcca gctcataaac   1260

accaacggta gctggcacat caacaggact gccctgaact gcaatgactc cctcaacacc   1320

gggtttcttg ccgcgctgtt ctacacgcac aagttcaacg cgtccggatg tccagagcgc   1380

ttggccagct gccgccccat tgacaagttc gatcaggggt ggggtcccat cacttatgct   1440

gagcagggcg gccaggacca gaggccttat tgctggcact acgcacctaa accatgtggt   1500

attgtatccg cgtcgaaggt gtgtggtcca gtgtattgtt tcaccccaag cccagttgta   1560

gtggggacga ccgatcggtt cggtgtccct acgtatagct gggggggagaa tgagacagac   1620

gtgctgctcc ttaacaacac gcggccgccg caaggcaact ggttcggctg tacgtggatg   1680
```

-continued

```
aacggcactg ggttcaccaa gacatgcggg ggccccccgt gtaacatcgg ggggggcggc   1740
aataacacct tgacctgccc tacggactgt ttccggaagc accccgcggc cacttacaca   1800
aaatgtggtt cgggaccttg gctgacaccc aggtgcttgg tagactaccc atacaggctc   1860
tggcactacc cctgcactgc caactttacc atcttcaagg ttaggatgta tgtagggggc   1920
gtggagcaca ggctcgatgc tgcatgcaat tggacccgag gggaacgttg caacttggag   1980
gatagggata gattggagct cagcccgcta ctgctgtcta caacagagtg gcaggtgctg   2040
ccctgttctt tcaccaccct accggctctg tccactggtt taattcatct ccatcagaac   2100
atcgtggacg tgcaatacct gtacggtata gggtcggcag ttgtttcctt tgcaatcaaa   2160
tgggactata tcgtgatact tttcctcctc ctggcggacg cgcgcgtctg tgcctgcttg   2220
tggatgatgc tgctgatagc ccaggccgag gccgccttag aaaacctggt ggtcctcaat   2280
gcggcgtccg tggccggagc gcatggcatt ctctccttcc ttgtgttctt ctgtgccgcc   2340
tggtacatca agggcaagct ggtccccggg gcagcatatg ctttctatgg agtatggccg   2400
ctgctcctgc ttctgctggc cttaccacca cgagcttacg ctatggagcg ggagatggct   2460
gcatcgtgcg gaggcgcggt gtttgtaggt ctggtactct tgactttgtc accatactat   2520
aaagagttcc tcgccaggct catatggtgg ttgcaatatt ttatcaccag agccgaggcg   2580
cacctgcaag tgtggatccc cccctcaac attcgggggg gccgcgatgc catcatcctc    2640
ctcgcgtgtg tagtccaccc agagctaatc tttgacatca ccaaactcct gctcgccata   2700
ctcggtccgc tcatggtgct ccaggctagc ataactcaag tgccgtactt cgtacgcgcc   2760
caagggctca ttcgtgcatg catgttggtg cggaaggtag ccgggggcca ttatgtccaa   2820
atggcctttg tgaagctgac cgcactgaca ggtacgtacg tttatgacca tctaactcca   2880
ctgcgggact gggcccacgc gggcctgcga gacctcgcgg tggcagtaga gcccgttgtc   2940
ttctctgaca tggagaccaa ggtcatcacc tggggggcag acaccgcagc gtgtggggac   3000
attatcttgg gtctacctgt ctccgcccga aggggtaggg agatacttct ggggccggcc   3060
gatagtcttg aagggcaggg gtggcggctc cttgctccca tcacggccta ttcccaacag   3120
acgcggggcc tacttggttg catcatcact agcctcacag gccgggacaa aaaccaagtc   3180
gagggggagg ttcaagtggt ctccaccgcg acacaatcct tcctggcgac ctgcgtcaat   3240
ggcgcgtgct ggactgtctt ccatggtgcc ggctcaaaga ccttagctgg cccaaaaggt   3300
ccaatcaccc agatgtacac taatgtagac ctggacctcg tcggctggca ggcgcccccc   3360
gggtcgcgtt ctctgacacc atgcacctgc ggcagctcag acctctattt ggtcacgaga   3420
catgctgatg tcattccggt gcgccggcgg ggcgacagta ggggaagcct actctctccc   3480
agacctgtct cctacttgaa aggctcctcg ggtggtccgc tgctctgccc ttcgaggcac   3540
gctgtgggca tcttccgggc tgctgtgtgc acccgggggg ttgcgaaggc ggtggatttc   3600
atacccgttg aatcaatgga aactactatg cggtctccgg tcttcacgga taactcatcc   3660
cccccggccg taccgcagac attccaagtg gcccatctac acgcccctac tggcagcggc   3720
aagagcacta aggtgccggc tgcatatgca gcccaagggt ataaggtgct cgtcctgaac   3780
ccgtccgttg ccgctacctt gggttttggg gcgtatatgt ctaaggcaca tggtatcgac   3840
cccaacatca gaactggggt aagggccatc accacgggcg cccctattac atactccacc   3900
tacggcaagt tccttgccga cggcggttgt tccgggggcg cctatgacat cataatatgt   3960
gatgagtgcc actcaactga ctcgactacc atcttgggca ttggcacagt cctggaccaa   4020
```

-continued

```
gcggagacgg ctggagcgcg gctcgtcgtg ctcgccaccg ctacgcctcc gggatcggtc   4080
accgtgccac accccaatat tgaggaggtg gccctgtcca acgctggaga aatccccttc   4140
tacggcaaag ccatccccat tgaggtcatc aagggggggaa gacatctcat tttctgccat   4200
tccaagaaga agtatgacga gctcgccgca aagctatcag ccctcggact taatgctgta   4260
gcatattatc ggggtcttga tgtgtccgtc ataccgacca acggagacgt cgttgtcgtg   4320
gcaacagacg ctctaatgac gggctttacc ggcgactttg actcagtgat cgactgtaac   4380
acatgtgtca cccagacagt cgatttcagc ctggatccca ccttcaccat cgagacgacg   4440
accgtgcccc aagacgcagt ggcgcgatca cagcggcggg gtaggactgg taggggcagg   4500
agaggcatct acaggtttgt gactccagga gaacggccct cgggcatgtt cgattcctcg   4560
gtcctgtgtg agtgctatga cgcgggctgt gcttggtacg agctcacgcc tgctgagacc   4620
tcggttaggt tgcgggctta cctgaataca ccagggttgc ccgtctgcca ggaccatctg   4680
gagttttggg agagcgtctc cacaggcctc acccacatag atgcccattt tctgtcccag   4740
actaaacagg caggagacaa cttcccctac ctggtagcat accaagccac agtgtgcgcc   4800
agagctcaag ctccacctcc atcatgggat caaatgtgga agtgtctcat acggctcaaa   4860
cccacgctgc acgggccaac acccctgctg tataggctag gagccgtcca aaatgagatc   4920
accctcacac accccatgac caaattcatc atggcatgca tgtcggctga cctggaggtc   4980
gtcactagca cctgggtgct agtaggcgga gtccttgcag ctctggctgc atattgcttg   5040
acaacaggca gtgtggtcat tgtgggtagg atcatcttgt ccgggaggcc ggctgttatt   5100
cccgacaggg aagtcctcta ccgggagttc gatgagatgg aagagtgcgc ctcacacctc   5160
ccttacatcg aacagggaat gcagcttgcc gagcaattca agcagaaggc gctcggattg   5220
ctgcaaacag ccaccaagca agcggaggct gctgctcccg tggtagaatc caagtggcga   5280
gcccttgaga ccttctgggc gaagcacatg tggaatttca tcagcgggat acagtaccta   5340
gcaggcttgt ccactctgcc tgggaacccc gcgatagcat cactgatggc attcacagcc   5400
tctatcacca gcccgctctc cacccagaat accctattat ttaacatctg gggggggatgg   5460
gtggctgccc aactcgcccc ccccagtgct gcttcggctt tcgtgggcgc cggtatcgcc   5520
ggtgcggctg tcggcagcat aggtcttggg aaggtgcttg tggacatctt ggcgggatat   5580
ggggcagggg tggctggcgc gctcgtagct tttaagatca tgagcggcga ggtgccctcc   5640
accgaggacc tggttaactt actccctgcc atcctctctc ccggcgccct agtcgtcggg   5700
gtcgtgtgcg cagcaatact gcgtcggcac gtgggcccgg gagagggggc tgtacagtgg   5760
atgaaccggc tgatagcgtt cgcctcgcgg ggtaaccacg tttcccccgc gcactatgtg   5820
cctgagagcg acgctgcggc gcgtgttact cagatcctct ccggccttac catcactcag   5880
ctgctgaaga ggcttcacca ctggatcaat gaggactgct ccacgccatg ctccggttcg   5940
tggctaaggg atgtttggga ctggatatgc acggtgttga ctgacttcaa gacctggctc   6000
cagtccaagc tcctgccgcg gttaccgggg gtccctttct tctcgtgtca acgcgggtac   6060
aagggagtct ggcgggggga cggtatcatg cagaccacct gcccgtgtgg agcacagatc   6120
accggacatg tcaaaaacgg ttccatgagg atcgtcgggc ctaaaacctg cagcagcacg   6180
tggcatggaa cgttccccat caacgcatac accacaggcc catgcgcacc ctccccggcg   6240
ccaaactatt ccagggcgct atggcgggtg gccgctgagg agtacgtgga ggttacgcgg   6300
gtgggggatt tccactacgt gacgggcatg accactgaca acgtaaagtg cccatgccag   6360
gttccggccc ctgaattctt cactgaggtg gatggagtgc ggttgcacag gtacgctccg   6420
```

-continued

```
gcgtgcaaac ccctcctacg ggaggaggtc acattccagg ttgggctcaa ccaatacctg   6480
gttgggtcac agctcccatg cgagcccgaa ccggatgtag cagtgctaac ttccatgctt   6540
accgacccct cccacatcac agcagagacg gcaaagcgta ggctggctag gggtctccc   6600
ccctccttgg ccagttcttc agctagccag ttatctgcgc cttccttgaa ggcgacatgc   6660
actacccatc atgactcccc ggacgttgac ctcatcgagg ccaacctcct gtggcggcag   6720
gagatgggcg ggaacatcac ccgcgtggag tcagagaata aggtagtaat tttggactct   6780
ttcgatccgc tccgagcgga ggaggacgag agggaaccat ccgttgcggc ggagatcttg   6840
cggaaaacca agaggttccc cccggcgatg cccatatggg cacgcccgga ttacaaccct   6900
ccgttgctag agtcctggaa agacccggac tacgtccctc cggtggtaca cgggtgcccg   6960
ctaccaccta ccaaagctcc tccgatacca cccccacgga gaaagaggac ggtagtcctg   7020
acagagtcca ctgtgtcttc tgccttggcg gagcttgcta ctaagacctt tggcagctcc   7080
gggtcgtcgg ccgtcgacag cggcacggca actgctcctc ccgaccaggc ttccgacgac   7140
ggcgaccaag gatctgacgt tgagtcgtat tcctccatgc cccctcttga gggagagccg   7200
ggggaccccg atctcagcga cggtcttggg tctaccgtga gcgaggaggc cggtgaggac   7260
gtcatctgct gctcaatgtc ctacacatgg acaggcgcct tgatcacgcc atgcgccgcg   7320
gaggaaagca agttgcccat caacccgttg agcaactctt tgttgcgtca ccacaacatg   7380
gtctatgcta caacatcccg cagcgcaggc ctacggcaga agaaggtcac ctttgacaga   7440
ctgcaagtcc tggacgacca ctaccgggac gtgctcaagg agatgaaggc gaaggcgtcc   7500
acagttaagg ctaaactcct atccatagaa gaagcctgta agctgacgcc cccacattcg   7560
gccagatcca aatttggcta tggggcaaag gacgtccgga acctatccag caaggccgtt   7620
aaccacatcc gctccgtgtg gaaggacttg ctggaagaca ctgagacacc aattgacacc   7680
accgtcatgg caaaaagtga ggttttctgc gtccaaccag agaaaggagg ccgcaagcca   7740
gctcgcctta tcgtattccc agacttgggg gttcgtgtat gcgagaagat ggccctttat   7800
gacgtggtct ccacccttcc tcaggccgtg atgggctcct catacggatt ccagtactcc   7860
cctggacagc gggtcgagtt cctggtgaat gcctggaaat caaagaaatg ccctatgggc   7920
ttttcatatg acacccgctg ttttgactcg acagtcactg agagtgacat ccgtgttgag   7980
gagtcaattt accaatgttg tgacttggcc cccgaagcca gacaggccat aaagtcgctc   8040
acagagcggc tttacattgg gggtcccctg accaattcaa aagggcagaa ctgtggctat   8100
cgccggtgcc gcgcgagtgg cgtgctgacg accagctgcg gtaataccct tacatgttac   8160
ttgaaggcct ctgcagcctg tcgagctgca aagctccggg actgcacgat gctcgtgaac   8220
ggagacgacc tcgtcgtcat ctgtgagagt gcgggaaccc aagaggatga ggcgaaccta   8280
cgagtcttca cggaggctat gactaggtat tctgcccccc ccggggaccc gccccgacca   8340
gaatacgact tggagctaat aacatcatgt tcctccaatg tgtcggtcgc gcacgatgca   8400
tctggcaaaa gggtatacta cctcacccgc gacccctcca ccccccttgc acgggctgcg   8460
tgggagacag ctagacacac tccagttaat tcctggctag gcaacatcat tatgtatgcg   8520
cccaccttat gggcaaggat gattctgatg acccatttct tctccatcct tctagcccag   8580
gagcaacttg aaaaagccct ggattgccag atctacgggg cctgttactc cattgagcca   8640
cttgacctac ctcagatcat tgaacgactc catggtctta gcgcattttc actccatagt   8700
tactctccag gtgagatcaa tagggtggct tcatgcctca ggaaacttgg ggtaccaccc   8760
```

ttgcgagtct ggagacatcg ggccagaagt gtccgcgcta agctgctgtc ccaggggggg 8820
agggctgcca cttgtggtaa gtacctcttc aactgggcag taaggaccaa gctcaaactc 8880
actccaatcc cggcagcgtc ccagttggac ttgtccagct ggttcgtggc tggttacagc 8940
gggggagaca tatatcacag cctgtctcgt gcccgacccc gctggttcat gttgtgccta 9000
ctcctacttt cagtaggggt aggcatctac ctgctcccca accgataa 9048

<210> SEQ ID NO 4
<211> LENGTH: 849
<212> TYPE: DNA
<213> ORGANISM: Vaccinia virus

<400> SEQUENCE: 4
gatgatgatg atgatgatga tgatgatgat gtcatagacg atgatgatta taatccaaaa 60
cccactccga taccggagcc tcaccctaga ccaccgtttc ccagacatga atatcataag 120
aggccgaaag ttcttcctgt agaagaacct gatcctgtca aaaaagacgc ggatcgtata 180
agacttgata atcatatatt aaacacattg gatcataatc ttaattccat cggacactat 240
tgttgtgata cagcagcagt tgataggtta gaacatcaca ttgaaacatt gggacaatat 300
gcagtaatac tagcaagaaa gataaatatg caaacattac tgttcccatg gccattacct 360
actgtccatc cacatgcgat agatggtagt attccgccac atgggagatc tacgatctta 420
taattacacg attgtagtta agttttgaat aaaatttttt tataataaat agaggtcacg 480
aacctcgact ctagaggatc ccattgtgaa aaattgaaaa actagtctaa tttattgcac 540
ggtgtgaaaa attgaaaaac tagtctaatt tattgcacgg tgtgaaaaat tgaaaaacta 600
gtctaattta ttgcacggtg tgaaaaattg aaaaactagt ctaatttatt gcacggtgtg 660
aaaaattgaa aaactagtct aatttattgc acggtgtgaa aaattgaaaa actagtctaa 720
tttattgcac ggtgtgaaaa attgaaaaac tagtctaatt tattgcacgg tgtgaaaaat 780
tgaaaaacta gtctaattta ttgcacggtg tgaaaaattg aaaaactagt taatttattg 840
cacggtgtg 849

<210> SEQ ID NO 5
<211> LENGTH: 88
<212> TYPE: DNA
<213> ORGANISM: Artificial
<220> FEATURE:
<223> OTHER INFORMATION: Synthetic DNA

<400> SEQUENCE: 5
gggcggccct gcaggtaata cgactcacta tagggcgtag accgtgcatc atgagcacaa 60
atcctaaacc ccaaagaaaa accaaacg 88

<210> SEQ ID NO 6
<211> LENGTH: 57
<212> TYPE: DNA
<213> ORGANISM: Artificial
<220> FEATURE:
<223> OTHER INFORMATION: Synthetic DNA

<400> SEQUENCE: 6
gggcggcgcg atcgcctatc attaaaggag ccgccacccc tgcccttcaa gactatc 57

<210> SEQ ID NO 7
<211> LENGTH: 83
<212> TYPE: DNA
<213> ORGANISM: Artificial

<220> FEATURE:
<223> OTHER INFORMATION: Synthetic DNA

<400> SEQUENCE: 7
gggcggccct gcaggtaata cgactcacta tagggcgtag accgtgcatc atgacgcggc 60
cgccgcaagg caactggttc ggc 83

<210> SEQ ID NO 8
<211> LENGTH: 51
<212> TYPE: DNA
<213> ORGANISM: Artificial
<220> FEATURE:
<223> OTHER INFORMATION: Synthetic DNA

<400> SEQUENCE: 8
gggcggcgcg atcgcctatc attatcggtt ggggagcagg tagatgccta c 51

<210> SEQ ID NO 9
<211> LENGTH: 23
<212> TYPE: DNA
<213> ORGANISM: Artificial
<220> FEATURE:
<223> OTHER INFORMATION: Synthetic DNA

<400> SEQUENCE: 9
ggtcttatat acaccgagta agg 23

<210> SEQ ID NO 10
<211> LENGTH: 20
<212> TYPE: DNA
<213> ORGANISM: Artificial
<220> FEATURE:
<223> OTHER INFORMATION: Synthetic DNA

<400> SEQUENCE: 10
tcaggaaaga cagccatagc 20

<210> SEQ ID NO 11
<211> LENGTH: 22
<212> TYPE: DNA
<213> ORGANISM: Artificial
<220> FEATURE:
<223> OTHER INFORMATION: Synthetic DNA

<400> SEQUENCE: 11
catcacattg aaacattggg ac 22

<210> SEQ ID NO 12
<211> LENGTH: 20
<212> TYPE: DNA
<213> ORGANISM: Artificial
<220> FEATURE:
<223> OTHER INFORMATION: Synthetic DNA

<400> SEQUENCE: 12
gatttgtgct catgatgcac 20

<210> SEQ ID NO 13
<211> LENGTH: 23
<212> TYPE: DNA
<213> ORGANISM: Artificial
<220> FEATURE:
<223> OTHER INFORMATION: Synthetic DNA

<400> SEQUENCE: 13

```
ccgaaccaca ttttgtgtaa gtg                                            23


<210> SEQ ID NO 14
<211> LENGTH: 18
<212> TYPE: DNA
<213> ORGANISM: Artificial
<220> FEATURE:
<223> OTHER INFORMATION: Synthetic DNA

<400> SEQUENCE: 14

agtagagccc gttgtctt                                                  18


<210> SEQ ID NO 15
<211> LENGTH: 20
<212> TYPE: DNA
<213> ORGANISM: Artificial
<220> FEATURE:
<223> OTHER INFORMATION: Synthetic DNA

<400> SEQUENCE: 15

tacctcttca actgggcagt                                                20


<210> SEQ ID NO 16
<211> LENGTH: 21
<212> TYPE: DNA
<213> ORGANISM: Artificial
<220> FEATURE:
<223> OTHER INFORMATION: Synthetic DNA

<400> SEQUENCE: 16

ctagttctga gaaaccagag g                                              21


<210> SEQ ID NO 17
<211> LENGTH: 10
<212> TYPE: PRT
<213> ORGANISM: Artificial
<220> FEATURE:
<223> OTHER INFORMATION: Synthetic peptide

<400> SEQUENCE: 17

Leu Met Gly Tyr Ile Pro Leu Val Gly Ala
1               5                   10


<210> SEQ ID NO 18
<211> LENGTH: 8
<212> TYPE: PRT
<213> ORGANISM: Artificial
<220> FEATURE:
<223> OTHER INFORMATION: Synthetic peptide

<400> SEQUENCE: 18

Gly His Arg Met Ala Trp Asp Met
1               5


<210> SEQ ID NO 19
<211> LENGTH: 10
<212> TYPE: PRT
<213> ORGANISM: Artificial
<220> FEATURE:
<223> OTHER INFORMATION: Synthetic peptide

<400> SEQUENCE: 19

Gly Gly Pro Pro Cys Asp Ile Gly Gly Val
1               5                   10


<210> SEQ ID NO 20
```

-continued

```
<211> LENGTH: 10
<212> TYPE: PRT
<213> ORGANISM: Artificial
<220> FEATURE:
<223> OTHER INFORMATION: Synthetic peptide

<400> SEQUENCE: 20

Gly Gly Pro Pro Cys Asn Ile Gly Gly Gly
1               5                   10
```